US011944731B2

(12) United States Patent
Lee et al.

(10) Patent No.: US 11,944,731 B2
(45) Date of Patent: Apr. 2, 2024

(54) DIALYZER CONTROL APPARATUS AND DRIVING METHOD THEREOF

(71) Applicant: UNIVERSITY INDUSTRY FOUNDATION, YONSEI UNIVERSITY WONJU CAMPUS, Wonju-si (KR)

(72) Inventors: Yong Heum Lee, Wonju-si (KR); Na Ra Lee, Gimhae-si (KR); Soo Yong Lee, Wonju-si (KR); Ja Woo Lee, Wonju-si (KR)

(73) Assignee: UNIVERSITY INDUSTRY FOUNDATION, YONSEI UNIVERSITY WONJU CAMPUS, Wonju-si (KR)

( * ) Notice: Subject to any disclaimer, the term of this patent is extended or adjusted under 35 U.S.C. 154(b) by 748 days.

(21) Appl. No.: 16/953,750

(22) Filed: Nov. 20, 2020

(65) Prior Publication Data

US 2021/0069398 A1   Mar. 11, 2021

Related U.S. Application Data

(63) Continuation of application No. PCT/KR2019/005692, filed on May 13, 2019.

(30) Foreign Application Priority Data

May 23, 2018 (KR) .......... 10-2018-0058118

(51) Int. Cl.
*A61M 1/16* (2006.01)
*A61M 1/36* (2006.01)

(52) U.S. Cl.
CPC ........ *A61M 1/1601* (2014.02); *A61M 1/3618* (2014.02); *A61M 2202/0429* (2013.01);
(Continued)

(58) Field of Classification Search
CPC .............. A61M 1/1601; A61M 1/3618; A61M 2202/0429; A61M 2202/0433;
(Continued)

(56) References Cited

U.S. PATENT DOCUMENTS 5,788,624 A * 8/1998 Lu ............................ A61N 2/06
600/15
6,794,194 B2 * 9/2004 Fava .................... A61M 1/3641
436/66
(Continued)

FOREIGN PATENT DOCUMENTS

AU   2014204314 B2 *  3/2018  .............. A61M 1/16
JP       05329205 A  * 12/1993
(Continued)

OTHER PUBLICATIONS

International Search Report—PCT/KR2019/005692 dated Aug. 12, 2019.
(Continued)

*Primary Examiner* — Susan S Su
*Assistant Examiner* — Ted Yang
(74) *Attorney, Agent, or Firm* — CANTOR COLBURN LLP

(57) ABSTRACT

A dialyzer control apparatus includes a magnetic field generator which is disposed on an outer surface of a dialyzer which removes wastes from a blood flowing therein and generates a magnetic field; and a controller which controls the magnetic field generator to perform a magnetic field stimulation on the blood flowing into the dialyzer. The magnetic field stimulation may be a stimulation related to the improvement of the Rouleaux formation for the red blood cells in the blood.

20 Claims, 21 Drawing Sheets

(52) U.S. Cl.
CPC . *A61M 2202/0433* (2013.01); *A61M 2230/20* (2013.01); *A61M 2230/50* (2013.01)

(58) Field of Classification Search
CPC .......... A61M 2230/20; A61M 2230/50; A61M 1/16; A61M 1/3672; A61M 1/3609; A61M 2205/057; A61M 2205/3368; A61M 1/362; A61N 2/02
See application file for complete search history.

(56) References Cited

U.S. PATENT DOCUMENTS

| | | | | |
|---|---|---|---|---|
| 9,002,655 | B2* | 4/2015 | Bene | A61M 1/1605 703/11 |
| 11,406,840 | B2* | 8/2022 | Tao | A61N 2/02 |
| 2002/0198435 | A1* | 12/2002 | Paturu | A61F 5/41 600/15 |
| 2003/0138961 | A1* | 7/2003 | Fava | A61M 1/3639 436/66 |
| 2003/0171640 | A1* | 9/2003 | Canedo | A61N 2/008 600/9 |
| 2010/0280303 | A1* | 11/2010 | Dietz | A61M 60/216 600/15 |
| 2014/0255906 | A1* | 9/2014 | Dietz | C12N 13/00 435/307.1 |
| 2014/0302482 | A1* | 10/2014 | Dietz | C12M 41/42 435/307.1 |
| 2016/0151639 | A1* | 6/2016 | Scharf | A61N 5/0624 607/92 |
| 2021/0069398 | A1* | 3/2021 | Lee | A61M 1/3672 |
| 2021/0283410 | A1* | 9/2021 | Tao | A61M 1/36 |

FOREIGN PATENT DOCUMENTS

| | | | |
|---|---|---|---|
| KR | 20080104070 | | 11/2008 |
| KR | 20100068738 | A * | 6/2010 |
| KR | 20100086078 | | 7/2010 |
| KR | 20130106977 | | 10/2013 |
| KR | 20130106977 | A * | 10/2013 |
| KR | 20140020682 | | 2/2014 |
| KR | 20140020682 | A * | 2/2014 |
| WO | WO-2019225895 | A1 * | 11/2019 .............. A61M 1/16 |

OTHER PUBLICATIONS

Korean Office Action—Korean Application No. 10-2018-0058118 dated Apr. 1, 2020, citing US 2014/0302482 and KR 10-2008-0104070.

* cited by examiner (a)                  (b)

(a)

(b)

(c)

(a)

(b)

(c)

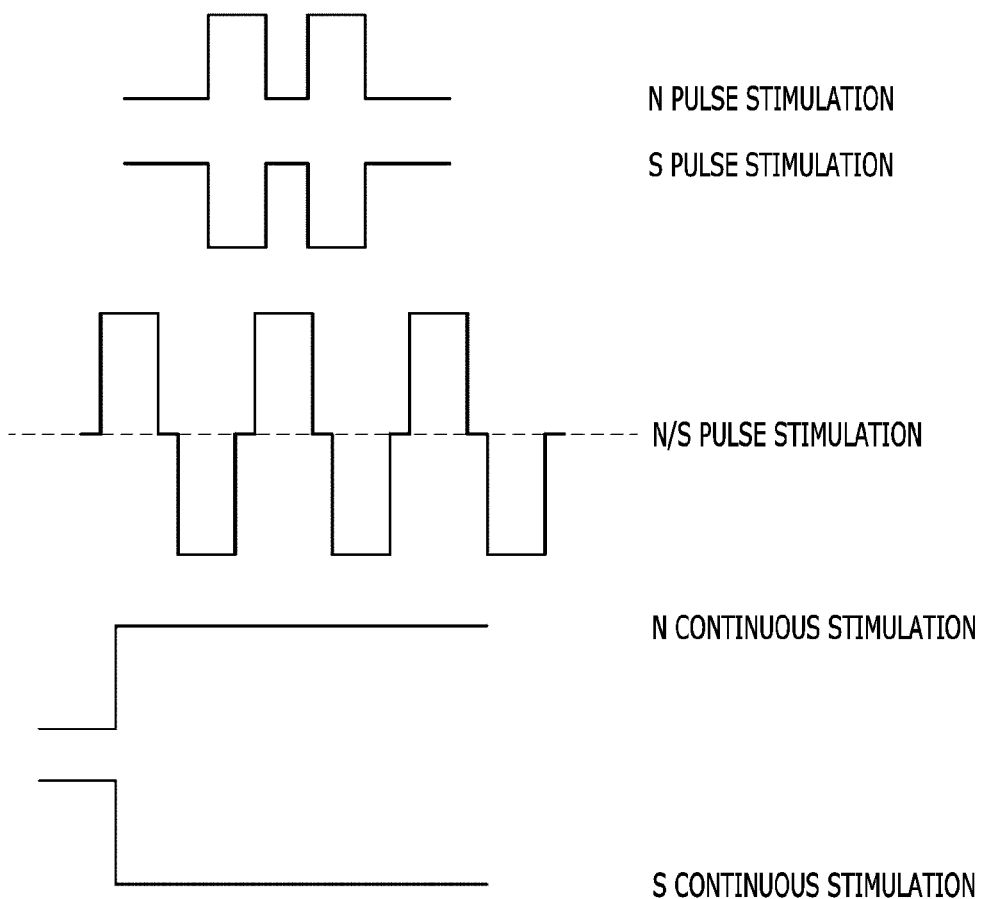

<STIMULATION RELATED TO BLOOD IONIZATION ACCELERATION>

<STIMULATION RELATED TO IMPROVEMENT OF ROULEAU FORMATION>

(a)

(b)

(a)

(b)

DIALYZER CONTROL APPARATUS AND DRIVING METHOD THEREOF

TECHNICAL FIELD

The present disclosure relates to a dialyzer control apparatus and a driving method thereof.

BACKGROUND

FIG. 1 is a view illustrating side view of a red blood cell (a) and a plan view of a red blood cell (b), and FIG. 2 is a view illustrating a hemoglobin molecule.

Referring to FIG. 1 and FIG. 2, the red blood cell (RBC, erythrocyte) is a disk (donut) shaped cell with a hollow in the center and a material which carries most of oxygen in the red blood cell is hemoglobin with iron ions.

A diameter of the red blood cell is approximately 7.2 to 8.4 μm and a thickness of the thickest part is 2 to 3 μm and a thickness in the center part is approximately 1 μm. Such a shape of the red blood cell has a larger blood cell surface area than a ball-shaped red blood cell, which increases the efficiency of gas exchange and makes it resistant to the change for an osmotic pressure or an external shock and makes the red blood cell membrane flexible so as to allow the red blood cells to easily pass through capillaries which are narrower than the diameter of the red blood cells (a diameter of the capillary is only approximately 4 μm).

The red blood cells have an ability to change their shape freely. In the presence of anti-γ globulinemia, a phenomenon that red blood cells are not evenly dispersed on the smear, but are overlapped as if stacked coins are scattered is referred to as Rouleaux formation (Geldrollen anordnung). Since this Rouleaux formation is one of the characteristics often found in patients with multiple myeloma and microglobulinemia, it is a standard for diagnosis of myeloma or microglobulinemia. A detailed description is as follows.

FIG. 3 is a view illustrating an example of the Rouleaux formation of the red blood cells.

Referring to FIG. 3, there are antibodies, globulins, and a thin layer with a low concentration of sugar around the red blood cells. When water in this layer is leaked to the outside due to the osmotic pressure (a), a layer with a rare material is instantaneously formed around the red blood cell to attach the peripheral red blood cells (b), and thus, the Rouleaux formation (c) in which the red blood cells stick together like a stack of coins occurs.

For example, due to diabetes, the higher the concentration of sugar in the blood or the more the plasma proteins such as globulin, the greater the difference in concentration between the plasma and the surface of the red blood cell. Therefore, in this case, the osmotic pressure is increased so that the possibility of the occurrence of Rouleaux formation may be increased.

Normal red blood cells have a negative charge on the surface so that the red blood cells are not gathered with each other due to the repulsive force. Accordingly, when the red blood cells are gathered with each other, it means a signal indicating that there is a problem somewhere in the user's body.

FIG. 4 is a view illustrating a normal red blood cell (a) and abnormal red blood cells (b and c) in which Rouleaux formation occurs.

Referring to FIG. 4, the normal red blood cells (a) do not overlap each other, but the red blood cells (b and c) with Rouleau formation are gathered to form a long clot.

As described above, when the Rouleaux formation in which the red blood cells form a long clot occurs, it is difficult to pass through the capillaries, the movement and the function of the blood are degraded, and the viscosity of the blood is increased, which may cause the cardiovascular disease. Therefore, a technology for improving the Rouleaux formation is required.

A background art of the present disclosure is disclosed in Korean Unexamined Patent Application Publication No. 10-2010-0086078.

DISCLOSURE OF THE INVENTION

Problems to be Solved by the Invention

The present disclosure is provided to solve the problems of the related art and an object of the present disclosure is to provide a dialyzer control apparatus which improves the Rouleaux formation of the red blood cell which not only degrades the movement and the function of the blood, but also increases the viscosity of the blood to cause the cardiovascular disease, and a driving method thereof.

However, objects to be achieved by various embodiments of the present disclosure are not limited to the technical objects as described above and other technical objects may be present.

Means for Solving the Problems

As a technical means to achieve the above-described technical object, a dialyzer control apparatus according to an exemplary embodiment of the present disclosure includes a magnetic field generator which is disposed on an outer surface of a dialyzer which removes wastes from a blood flowing therein to discharge and generates a magnetic field; and a controller which controls the magnetic field generator to perform magnetic field stimulation on the blood flowing into the dialyzer, and the magnetic field stimulation may be a stimulation related to the improvement of the Rouleaux formation for the red blood cells in the blood.

Further, the magnetic field stimulation may be a stimulation related to the blood ionization acceleration by binding oxygen to iron ions included in the hemoglobin of the red blood cells.

Further, the magnetic field stimulation may be a stimulation related to acceleration of at least one of anti-inflammatory, anti-cancer, and antimicrobial effects due to the generation of nitric oxide (NO) in the blood.

Further, the controller may control at least one of an intensity, a frequency, a time, a pattern, and a stimulation mode of a magnetic field as a type of magnetic field generated from the magnetic field generator.

Further, the controller controls the frequency of the magnetic field to any one of 8 Hz to 30 Hz and the magnetic field generator generates a magnetic field having a frequency of any one of 8 Hz to 30 Hz to perform a magnetic field stimulation on the blood.

Further, the dialyzer control apparatus according to an exemplary embodiment of the present disclosure may further include a hemoglobin level measuring unit which measures a hemoglobin level of red blood cells in the blood flowing into the dialyzer, and the controller may change a type of the magnetic field from a first type to a second type depending on whether the measured hemoglobin level is equal to or lower than a predetermined reference level.

Further, the dialyzer control apparatus according to an exemplary embodiment of the present disclosure may further include a core temperature measuring unit which measures a core temperature of the magnetic field generator, and the controller may control the type of the magnetic field by considering whether the measured core temperature is equal to or higher than a predetermined reference temperature.

Further, the controller may change at least one type of magnetic field at every predetermined time interval.

Further, the magnetic field generator may include a core having a through hole and a coil wound around the core.

Further, the magnetic field generator is disposed on an outer surface of the dialyzer such that the dialyzer is located to pass through a through hole of a core included in the magnetic field generator, the magnetic field generator includes a plurality of sub magnetic field generators disposed with an interval along a length direction of the dialyzer, and the controller may control the type of magnetic field generated from each of the plurality of sub magnetic field generators to be different from each other.

Further, the magnetic field generator includes one pair of magnetic field generators disposed to be opposite to each other with a circumference of the dialyzer therebetween and when there is a plurality of pairs of magnetic field generators disposed to be opposite to each other with the circumference, the controller may control the type of magnetic field generated from each of the plurality of pairs of magnetic field generators to be different from each other.

Further, the magnetic field generator includes a plurality of pairs of magnetic field generators disposed with an interval along a length direction of the dialyzer, and the controller may control the type of magnetic field generated from each of the plurality of pairs of magnetic field generators to be different from each other.

Further, when a first magnetic field generator between one pair of magnetic field generators generates an N pulse stimulation as a type of magnetic field, a second magnetic field generator between one pair of magnetic field generators generates an S pulse stimulation as a type of magnetic field and the controller may control one pair of magnetic field generators to allow the first magnetic field generator and the second magnetic field generator to alternately generate the N pulse stimulation and the S pulse stimulation according to a predetermined cycle.

Further, the dialyzer control apparatus according to an exemplary embodiment of the present disclosure may further include a distance adjusting unit which adjusts a distance between the one pair of magnetic field generators.

The controller may control the driving of the distance adjusting unit to adjust a type of the magnetic field generated from the one pair of magnetic field generators.

The magnetic field generator may generate a pulsed electro-magnetic field (PEMF).

In the meantime, a driving method of a dialyzer control apparatus according to an exemplary embodiment of the present disclosure may include controlling the magnetic field generator to perform a magnetic field stimulation on a blood flowing into a dialyzer which removes wastes from a blood flowing therein to discharge; and generating a magnetic field from the magnetic field generator provided to enclose an outer surface of the dialyzer according to the control.

Further, during the controlling, at least one of an intensity, a frequency, a time, a pattern, and a stimulation mode of a magnetic field may be controlled as a type of the magnetic field generated from the magnetic field generator.

The above-described solving means are merely illustrative but should not be construed as limiting the present disclosure. In addition to the above-described embodiments, additional embodiments may be further provided in the drawings and the detailed description of the present disclosure.

Effects of the Invention

According to the solving means of the present disclosure, a dialyzer control apparatus which controls the magnetic field generator to perform the magnetic field stimulation related to the improvement of the Rouleaux formation for the red blood cells in the blood flowing into the dialyzer is provided to effectively improve the Rouleaux formation of the red blood cells which not only degrades the movement and the function of the blood, but also increases the viscosity of the blood to cause the cardiovascular disease.

According to the solving means of the present disclosure, a dialyzer control apparatus which controls the magnetic field generator to perform the magnetic field stimulation on the blood flowing into the dialyzer is provided to improve the Rouleaux formation for the red blood cells in the blood, accelerate the blood ionization, and accelerate at least one of anti-inflammatory, anti-cancer, and antimicrobial effects.

However, the effect which can be achieved by the present disclosure is not limited to the above-described effects, there may be other effects.

BRIEF DESCRIPTION OF DRAWINGS

FIG. 8B is a view illustrating an example of a stimulation mode among types of magnetic field of a magnetic field generator which is controllable by a dialyzer control apparatus according to an exemplary embodiment of the present disclosure;

BEST MODE FOR CARRYING OUT THE INVENTION

Figure 1:
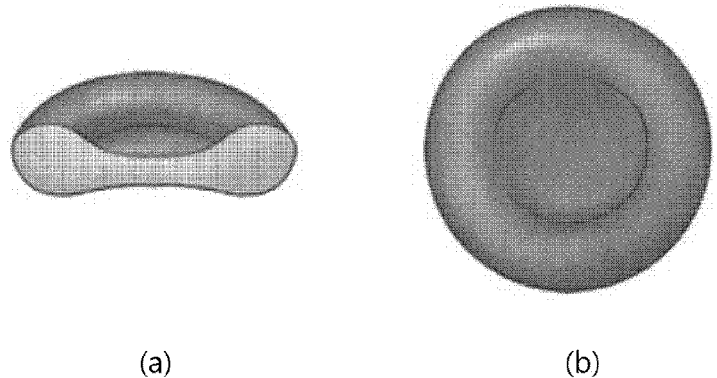
FIG. 1 is a view illustrating side view of a red blood cell (a) and a plan view of a red blood cell (b)
Figure 2:
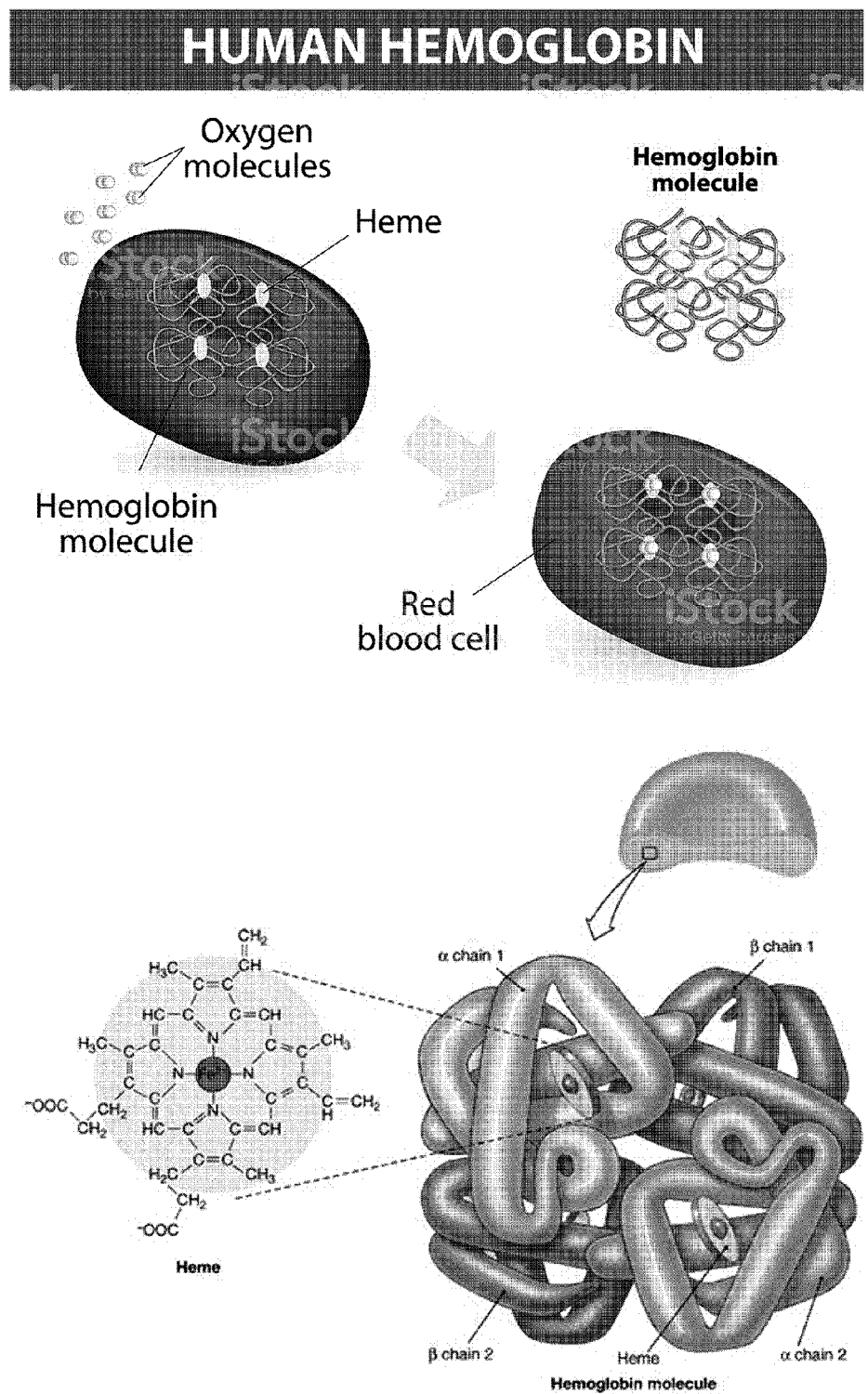
FIG. 2 is a view illustrating a hemoglobin molecule of a red blood cell.
Figure 3:
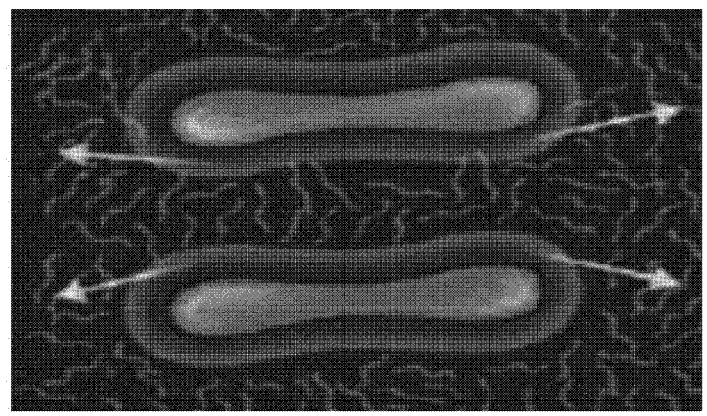
FIG. 3 is a view illustrating an example of the Rouleaux formation of the red blood cells.
Figure 3:
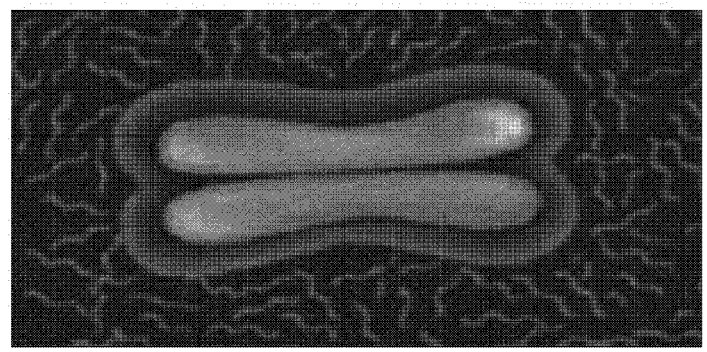
Figure 3:
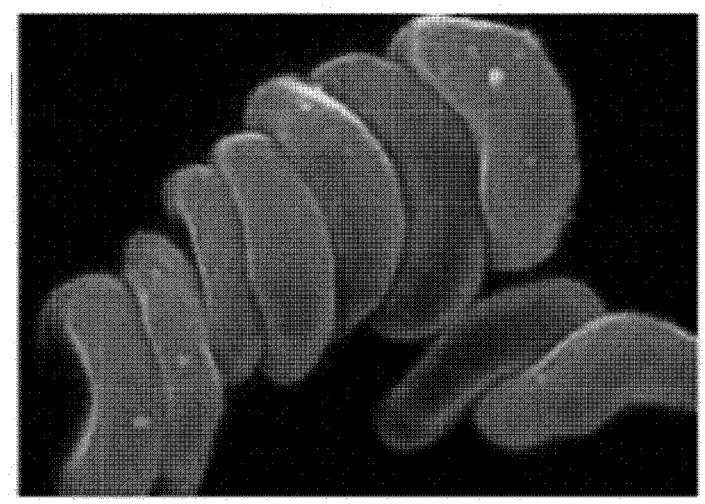
Figure 4:
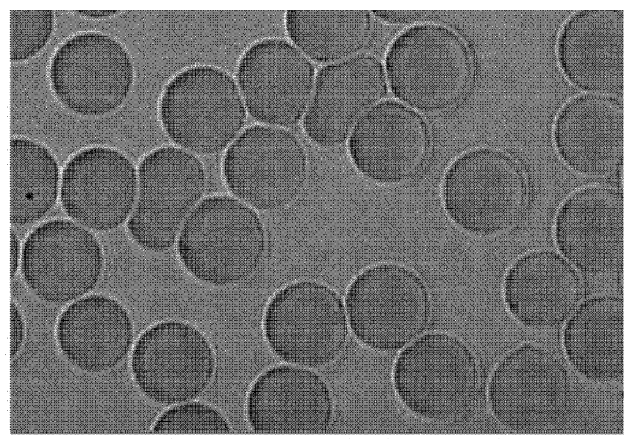
FIG. 4 is a view illustrating a normal red blood cell (a) and abnormal red blood cells (b and c) in which Rouleaux formation occurs.
Figure 4:
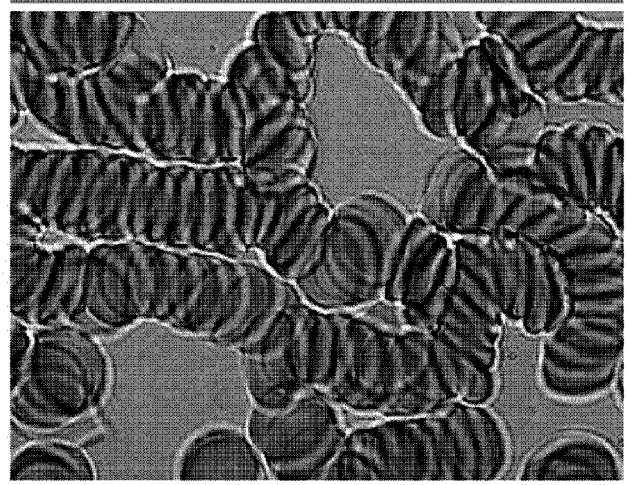
Figure 4:
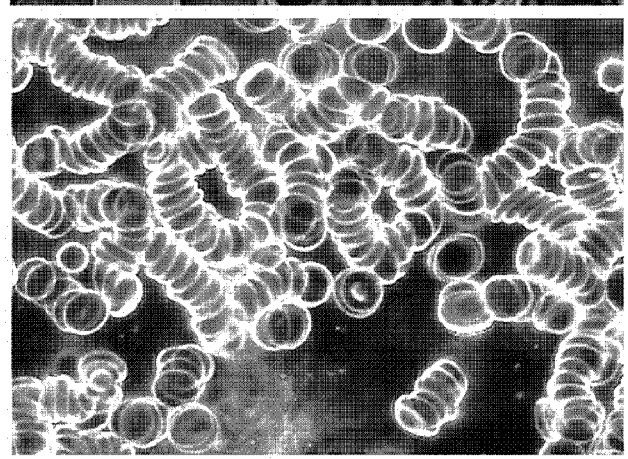

Hereinafter, the present disclosure will be described more fully hereinafter with reference to the accompanying drawings, in which exemplary embodiments of the present disclosure are shown. However, the present disclosure can be realized in various different forms, and is not limited to the embodiments described herein. Accordingly, in order to clearly explain the present disclosure in the drawings, portions not related to the description are omitted. Like reference numerals designate like elements throughout the specification.

Throughout this specification and the claims that follow, when it is described that an element is "coupled" to another element, the element may be "directly coupled" to the other element or "electrically coupled" or "indirectly coupled" to the other element through a third element.

Through the specification of the present disclosure, when one member is located "on", "above", "on an upper portion", "below", "under", and "on a lower portion" of the other member, the member may be adjacent to the other member or a third member may be disposed between the above two members.

In the specification of the present disclosure, unless explicitly described to the contrary, the word "comprise" and variations such as "comprises" or "comprising", will be understood to imply the inclusion of stated elements but not the exclusion of any other elements.

Figure 5:
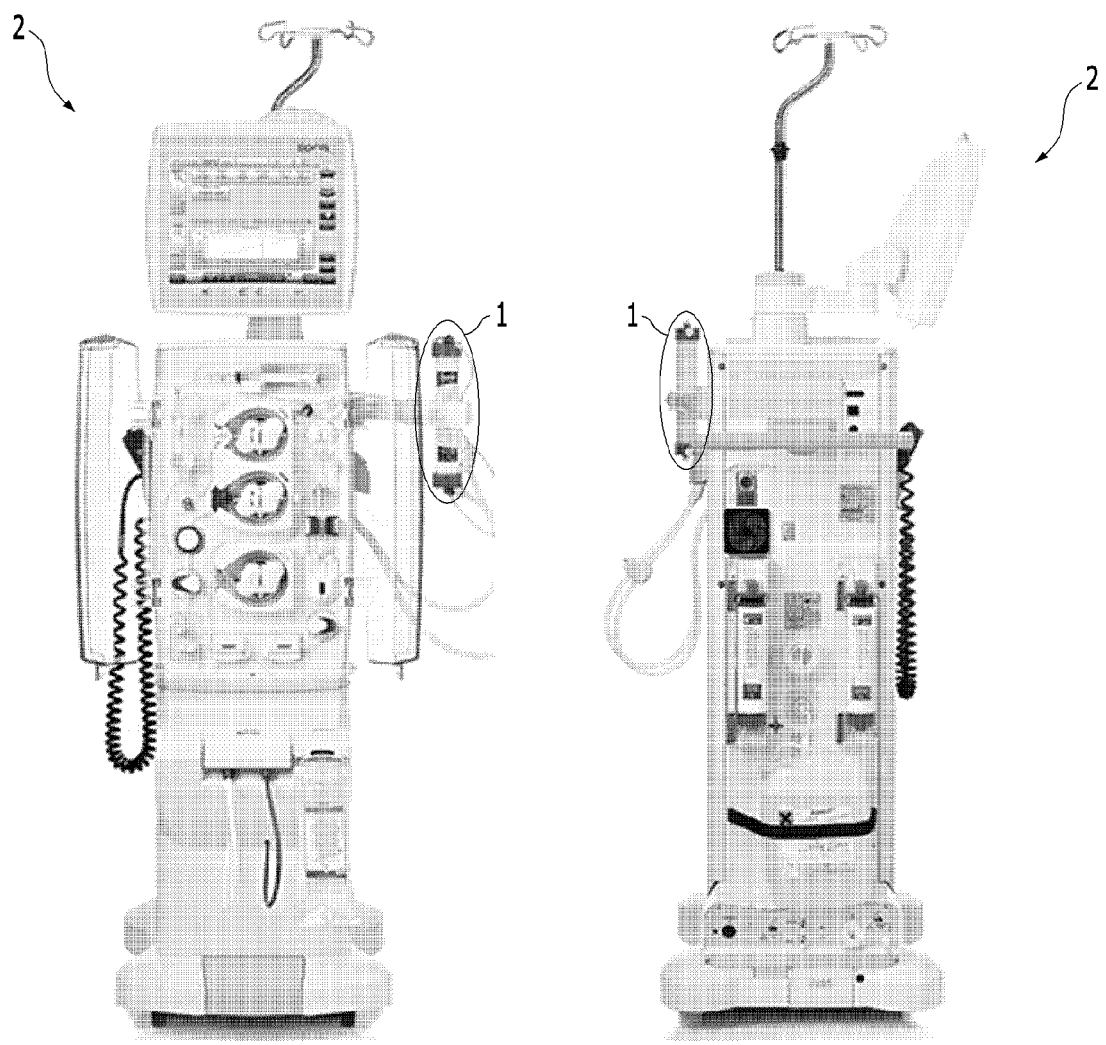
FIG. 5 is a view illustrating an example of a dialyzer equipped in a hemodialysis apparatus of the related art.
Figure 6:
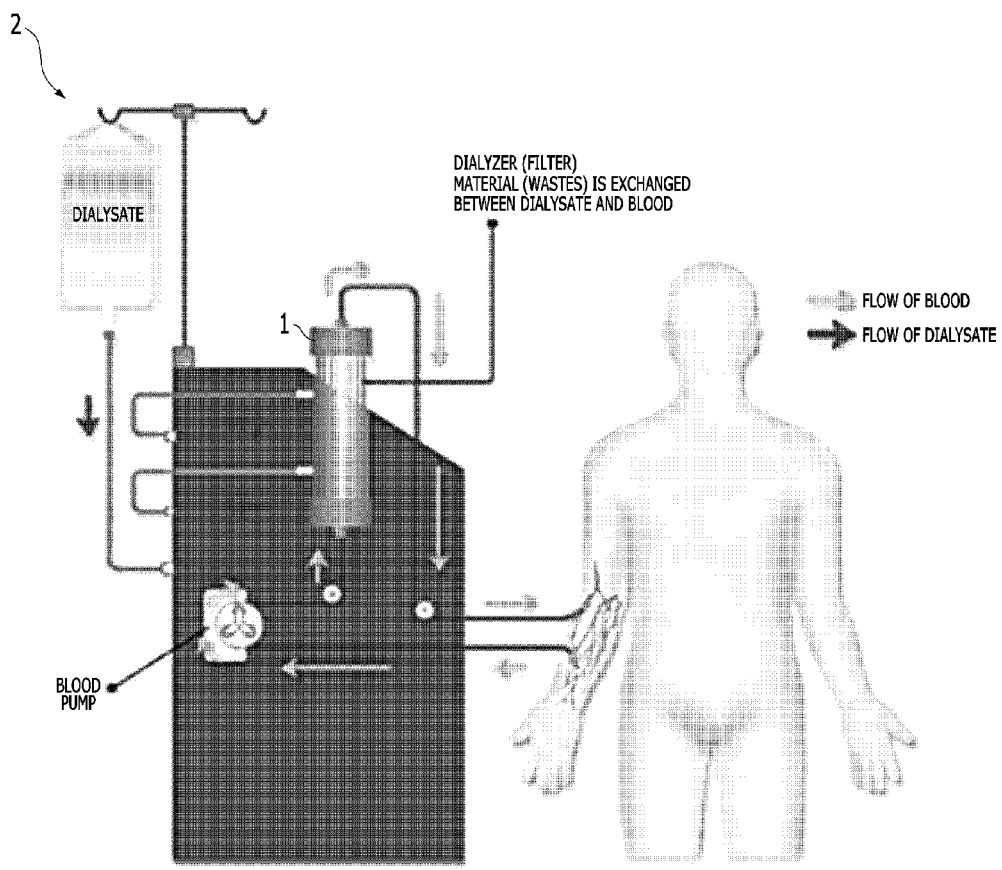
FIG. 6 is a view schematically explaining a hemodialysis principle using a dialyzer of a hemodialysis apparatus of the related art.

FIG. 5 is a view illustrating an example of a dialyzer (hemopurifier) 1 equipped in a hemodialysis apparatus 2 of the related art and FIG. 6 is a view schematically explaining a hemodialysis principle (method) using a dialyzer of a hemodialysis apparatus of the related art.

Referring to FIG. 5 and FIG. 6, the dialysis works on the principles of the diffusion of solutes and ultrafiltration of a solvent across a semipermeable membrane. Blood of a subject (patient) is pumped through a blood compartment of a dialyzer 1 to be in contact with a semipermeable membrane and a purified blood is returned to the body via a circuit. The ultrafiltration occurs due to the increase of a hydrostatic pressure generated in a dialyzer membrane.

The dialyzer 1 may be referred to as a tool serving as a filter in which a waste electrolyte is exchanged between the blood and a dialysate. For example, the dialyzer 1 may have two connection parts connected to the blood and two connection parts connected to the dialysate. Recently, as a dialyzer 1, a hollow-fiber dialyzer is mainly used and there may be thousands of thin hollow fibers in a cylinder of the hollow-fiber dialyzer.

When the blood extracted from the subject flows into the dialyzer 1, the blood is in contact with the dialysate in the dialyzer 1 so that wastes, excess electrolytes, and moisture move from the blood to the dialysate. Further, for example, heparin which is an anticoagulant is added to the blood coming out from the body to prevent the clotting and the blood from which wastes are filtered while passing through the dialyzer 1 is brought back into the body.

Hereinafter, a dialyzer for improving Rouleaux formation which improves the Rouleaux formation of the red blood cell by performing magnetic field stimulation on the blood flowing into the dialyzer 1 and a dialyzer control apparatus which controls the dialyzer for improving Rouleaux formation will be described in more detail.

Figure 7:
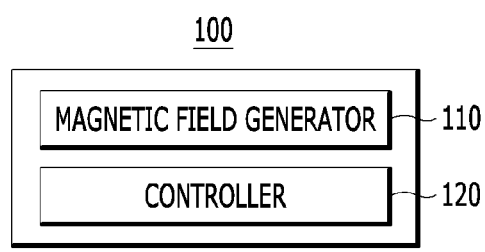
FIG. 7 is a block diagram illustrating a schematic configuration of a dialyzer control apparatus according to an exemplary embodiment of the present disclosure.
Figure 8A:
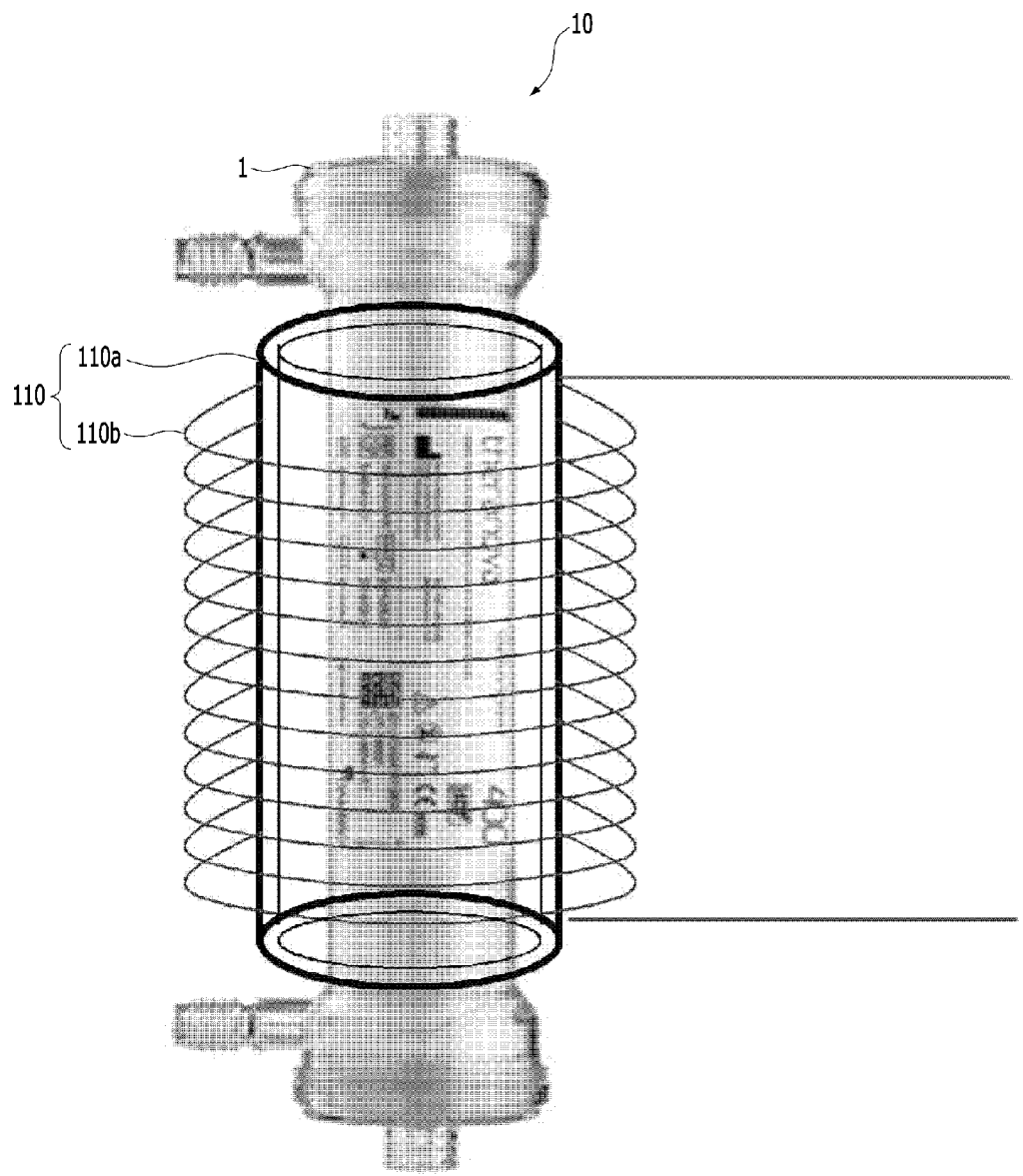
FIG. 8A is a view illustrating a dialyzer for improving Rouleaux formation including a magnetic field generator according to a first exemplary embodiment which is applied to a dialyzer control apparatus according to an exemplary embodiment of the present disclosure.

FIG. 7 is a block diagram illustrating a schematic configuration of a dialyzer control apparatus 100 according to an exemplary embodiment of the present disclosure. FIG. 8A is a view illustrating a dialyzer 10 for improving Rouleaux formation including a magnetic field generator 110 according to a first exemplary embodiment which is applied to a dialyzer control apparatus 100 according to an exemplary embodiment of the present disclosure. Hereinafter, the dialyzer control apparatus 100 according to an exemplary embodiment of the present disclosure will be simply referred to as the present apparatus 100 for the convenience of description.

Referring to FIG. 7 and FIG. 8A, the present apparatus 100 may include a magnetic field generator 110 and a controller 120.

The magnetic field generator 110 is disposed on an outer surface of the dialyzer 1 which removes wastes in the blood flowing therein to be brought out and generates a magnetic field(pulsed magnetic field). Here, as the dialyzer (hemopurifier) 1 with the magnetic field generator 110 formed on an outer surface, any of dialyzers which have been known in the related art or will be developed in the future may be applicable.

Further, for example, as illustrated in FIG. 8A, the dialyzer 1 including the magnetic field generator 110 is a dialyzer 10 proposed by the present disclosure (in other words, a dialyzer applied to the present apparatus) and may also be referred to as a dialyzer (hemopurifier) 10 for improving Rouleaux formation, a blood purifier 10 for improving Rouleaux formation, or the like. According to the above-description, the present apparatus 100 may be a dialyzer control apparatus which controls the dialyzer 10 for improving Rouleaux formation. Further, the magnetic field generator 110 included in the dialyzer 10 for improving Rouleaux formation may be formed with various structures (shapes), which will be described in more detail below.

The controller 120 may control the magnetic field generator 110 to perform the magnetic field stimulation on the blood flowing into the dialyzer 1. Further, the magnetic field stimulation may be a stimulation related to the improvement of the Rouleaux formation for the red blood cells in the blood. Further, the magnetic field stimulation may be a stimulation related to the blood ionization acceleration by binding oxygen to iron ions included in the hemoglobin of the red blood cells. Further, the magnetic field stimulation may be a stimulation related to acceleration of at least one of anti-inflammatory, anti-cancer, and antimicrobial effects due to the production of nitric oxide (NO) in the blood.

In other words, the controller 120 controls the magnetic field generator 110 so that the magnetic field generator 110 may generate the magnetic field so as to apply the magnetic field(pulsed magnetic field) to the blood flowing into the dialyzer 1 and the magnetic field stimulation on the blood may be performed by the magnetic field generated from the magnetic field generator 110.

In this case, the present apparatus 100 stimulates the blood with the magnetic field generated from the magnetic field generator 110 to improve the Rouleaux formation for the red blood cells in the blood. Further, the present apparatus 100 stimulates the blood with the magnetic field generated from the magnetic field generator 110 to allow the oxygen to be bond to the iron ions included in the hemoglobin of the red blood cells, thereby accelerating the blood ionization. Further, the present apparatus 100 stimulates the blood with the magnetic field generated from the magnetic field generator 110 to accelerate any one of anti-inflammatory, anti-cancer, and antimicrobial effects by generating nitric oxide (NO) in the blood. A specific description thereof will be made in more detail below.

The controller 120 may control at least one of an intensity (a magnetic flux density), a frequency, a time, a pattern, and a stimulation mode of a magnetic field as a type of magnetic field generated from the magnetic field generator 110. However, the present disclosure is not limited thereto, but the controller 120 may perform various controls related to all properties of the magnetic field as a type of magnetic field. For example, the controller 120 may control a current, a voltage, and the like as a type of magnetic field for forming an alternate magnetic field from the magnetic field generator 110 and also control a temperature of a core included in the magnetic field generator 110.

The magnetic field generator 110 may include a core 110a having a through hole and a coil 110b wound around the core 110a. For example, the core 110a may have a cylindrical shape, but is not limited thereto. For example, the core 110a may have a ferromagnetic substance, but is not limited thereto. The coil 110b may be provided so as to be wound around the core 110a and for example, may be a solenoid coil. The core 110a may be implemented to have various diameters. In this case, the term "diameter" may be broadly interpreted as referring to various widths rather than narrowly interpreted as a meaning of the diameter of a circular shape.

The magnetic field generator 110 may generate a pulsed electro-magnetic field (PEMF) as a time varying magnetic field. For example, when an AC current is applied (an alternating power is applied) under the control of the controller 120, the magnetic field generator 110 may generate a pulsed electro-magnetic field. Further, for example, the magnetic field generator 110 may generate a bidirectional alternating magnetic field (which may refer to alternating stimulation of an N pulse and an S pulse or N/S stimulation), but is not limited thereto and generate a magnetic field in various stimulation modes. Further, the controller 120 may apply a pulsed alternating power or a sine wave alternating power to the magnetic field generator 110. The magnetic field generator 110 may generate at least one of a pulsed magnetic field, a sine wave magnetic field, and an alternating magnetic field.

The magnetic field generator 110 may generate eddy currents by a weak time-varying magnetic field and the eddy currents may allow the magnetic field stimulation on the blood flowing into the dialyzer 1. In other words, the magnetic field stimulation may be performed on the blood (human tissue cell) of the subject to be dialyzed by the pulsed electromagnetic field (PEMF) generated from the magnetic field generator 110.

FIG. 8B is a view illustrating an example of a stimulation mode among types of a magnetic field of a magnetic field generator 110 which is controllable by a dialyzer control apparatus 100 according to an exemplary embodiment of the present disclosure.

Referring to FIG. 8B, the controller 120 may control the stimulation mode as a type of magnetic field of the magnetic field generator 110. For example, the stimulation mode may include an N pulse stimulation mode, an S pulse stimulation mode, an alternating stimulation mode of N pulse and S pulse (N/S stimulation), an N pulse continuous stimulation (N continuous stimulation) mode, and an S pulse continuous stimulation (S continuous) mode.

According to this, the controller 120 may control the stimulation mode of the magnetic field generator 110 to generate a magnetic field corresponding to any one stimulation of an N pulse stimulation, an S pulse stimulation, an alternating stimulation of N pulse and S pulse (N/S stimulation), an N pulse continuous stimulation, and an S pulse continuous stimulation from the magnetic field generator 110.

Figure 8C:
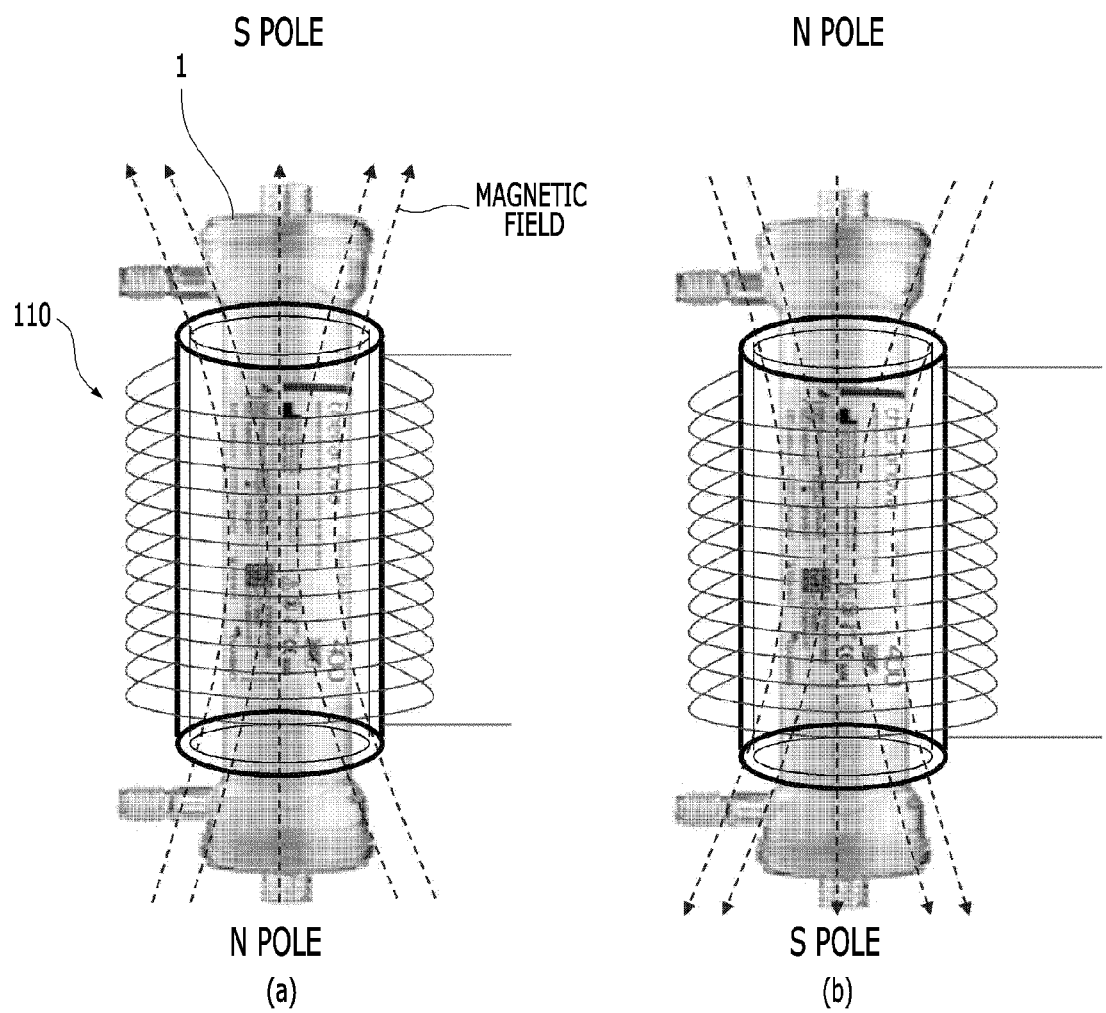
FIG. 8C is a view illustrating an example of a magnetic field generated from a magnetic field generator in a dialyzer control apparatus according to an exemplary embodiment of the present disclosure.

FIG. 8C is a view illustrating an example of a magnetic field generated from a magnetic field generator 110 in a dialyzer control apparatus 100 according to an exemplary embodiment of the present disclosure.

Referring to (a) of FIG. 8C, the controller 120 may control the magnetic field generator 110 so as to generate a magnetic field in which an N pole is formed at the lower side of the dialyzer 1 and an S pole is formed at the upper side of the dialyzer 1 (that is, a magnetic field is formed from the lower side to the upper side of the dialyzer), with reference to the drawing. Further, referring to (b) of FIG. 8C, the controller 120 may control the magnetic field generator 110 so as to generate a magnetic field in which an S pole is formed at the lower side of the dialyzer 1 and an N pole is formed at the upper side of the dialyzer 1 (that is, a magnetic field is formed from the upper side to the lower side of the dialyzer), with reference to the drawing.

The controller 120 may apply a physiologic frequency to the magnetic field generator 110.

For example, the physiologic frequency may refer to a frequency corresponding to any one of 8 Hz to 30 Hz.

In other words, the controller 120 may control the frequency of the magnetic field, among the types of the magnetic field generated from the magnetic field generator 110, to any one of 8 Hz to 30 Hz. In accordance with the control of the controller 120, the magnetic field generator 110 generates a magnetic field having any one frequency of 8 Hz to 30 Hz to perform the magnetic field stimulation on the blood flowing into the dialyzer 1.

According to an exemplary embodiment of the present disclosure, even though it is described that the frequency of the magnetic field is any one of 8 Hz to 30 Hz, the present disclosure is not limited thereto and various frequencies may be applied. For example, the magnetic field generator 110 may be controlled to generate a magnetic field with a frequency within a range of up to 300 Hz.

Further, the controller 120 may control the intensity (magnetic flux density) of the magnetic field, among the types of the magnetic field generated from the magnetic field generator 110, to any one of 250 Gauss (25 mT) to 350 Gauss (35 mT). Desirably, the controller 120 may control the intensity of the magnetic field generated from the magnetic field generator 110 to 300 Gauss (30 mT).

In the exemplary embodiment of the present disclosure, even though it is described that the intensity of the magnetic field generated from the magnetic field generator 110 is any one of 250 Gauss (25 mT) to 350 Gauss (35 mT), the present disclosure is not limited thereto and various intensities of the magnetic field may be applied. For example, the magnetic field generator 110 may be controlled to generate a magnetic field with an intensity within a range of up to 1000 Gauss (100 mT).

In the meantime, as described above, the magnetic field generator 110 may be controlled by the controller 120 to generate a magnetic field (for example, a pulsed electro-magnetic field: PEMF) to perform the magnetic field stimulation on the blood flowing into the dialyzer 1.

Figure 9A:
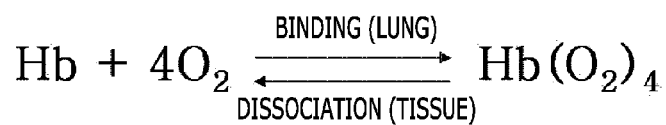
FIG. 9A is a view for explaining a stimulation related to blood ionization acceleration as an example of a magnetic field stimulation by a dialyzer control apparatus according to an exemplary embodiment of the present disclosure.
Figure 9A:
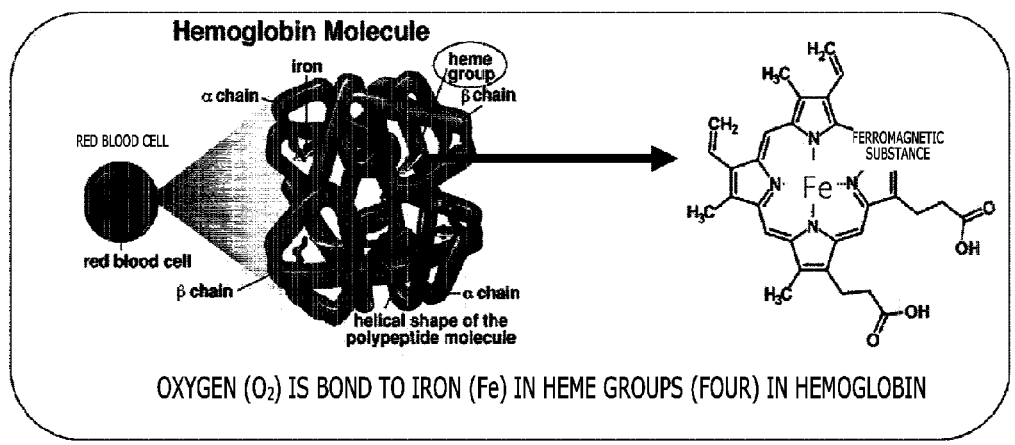

FIG. 9A is a view for explaining stimulation related to blood ionization acceleration as an example of a magnetic field stimulation by a dialyzer control apparatus according to an exemplary embodiment of the present disclosure.

Referring to FIG. 9A, when the magnetic field generator 110 generates a magnetic field for the blood flowing into the dialyzer 1, oxygen ($O_2$) may be coupled to irons (Fe) in hemo groups (four) in the hemoglobin of the red blood cells in the blood by the magnetic field generated from the magnetic field generator 110 and thus the blood ionization may be accelerated. In other words, the controller 120 may control the magnetic field generator 110 so as to generate a magnetic field which allows the oxygen to bind with the iron ions included in the hemoglobin of the red blood cells in the blood to accelerate the blood ionization.

When the magnetic field generator 110 generates a pulsed electro-magnetic field by the control of the controller 120, an alternating magnetic force (Lorenz force) may be applied to the iron ions in the hemoglobin of the red blood cells in the blood flowing into the dialyzer 1 and thus the red blood cells in the Rouleaux formation state are freely separated to improve the Rouleaux formation and accelerate the blood ionization.

The present apparatus 100 performs the magnetic field stimulation related to the blood ionization acceleration on the blood flowing into the dialyzer 1 by means of the magnetic field generator 110 to provide effects such as blood vessel expansion, blood flow improvement, blood viscosity improvement, and blood purification.

Figure 9B:
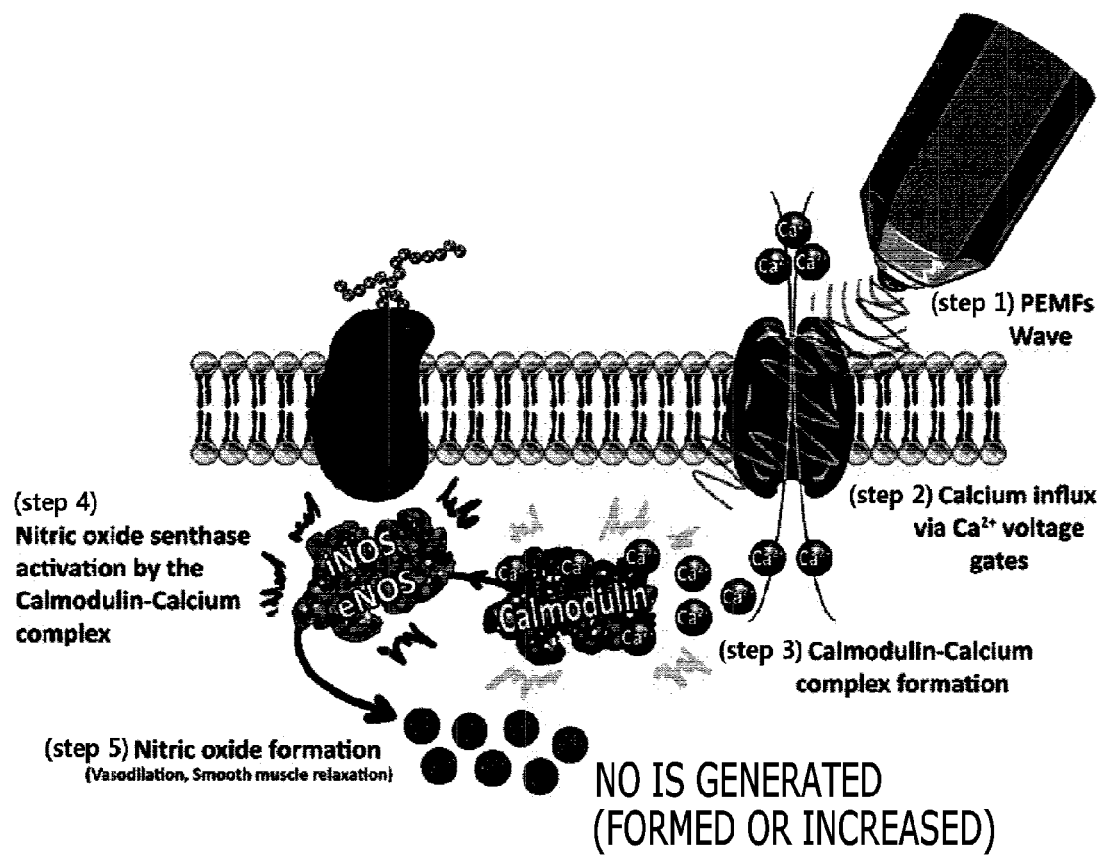
FIG. 9B is a view for explaining a stimulation related to generation of NO as an example of a magnetic field stimulation by a dialyzer control apparatus according to an exemplary embodiment of the present disclosure.

FIG. 9B is a view for explaining stimulation related to generation of nitric oxide (NO) (for example, stimulation related to acceleration of at least one of anti-cancer and antimicrobial effects) as an example of a magnetic field stimulation by a dialyzer control apparatus according to an exemplary embodiment of the present disclosure.

Referring to FIG. 9B, the magnetic field generator 110 may generate a magnetic field (for example, PEMFs wave) to the blood flowing into the dialyzer 1 (step 1). In this case, calcium influx via $Ca^{2+}$ voltage gate may be performed by the magnetic field generated from the magnetic field generator 110 (step 2). By doing this, a calmodulin-calcium complex is formed (step 3) and nitric oxide synthase (eNOS) is activated by the calmodulin-calcium complex (step 4) to form nitric oxide (step 5).

In this case, when step 1 to step 5 are performed, $Ca^{2+}$ and CaM are coupled to generate $Ca^{2+}$ CaM (in other words, $Ca^{2+}$/CaM). $Ca^{2+}$ CaM is generated so that muscle tissue contraction/relaxation effect may be provided. Further, $Ca^{2+}$ CaM and S are coupled to generate nitric oxide (NO). The nitric oxide (NO) is generated so that an effect of increasing blood and lymph fluid as an anti-inflammatory agent and an effect of reducing pain and edema may be provided. The generated NO may be applied as growth factors which increase cGMP. The effects such as FGF-2 (VEGF) angiogenesis (blood vessel formation), TNF-α collagen/granulation, and TGF-β remodeling may be provided by the generated NO.

That is, the nitric oxide may be generated (formed or increased) in the blood by the magnetic field generated from the magnetic field generator 110 and thus at least one of anti-inflammatory, anti-cancer, and antimicrobial effects may be accelerated. In other words, the controller 120 may control the magnetic field generator 110 to generate a magnetic field which generates nitric oxide (NO) in the blood to accelerate at least one of anti-inflammatory, anti-cancer, and antimicrobial effects.

The present apparatus 100 may perform the magnetic field stimulation related to acceleration of at least one of anti-inflammatory, anti-cancer, and antimicrobial effects on the blood flowing into the dialyzer 1 by means of the magnetic field generator 110 to provide edema and inflammation treatment effects.

Figure 9C:
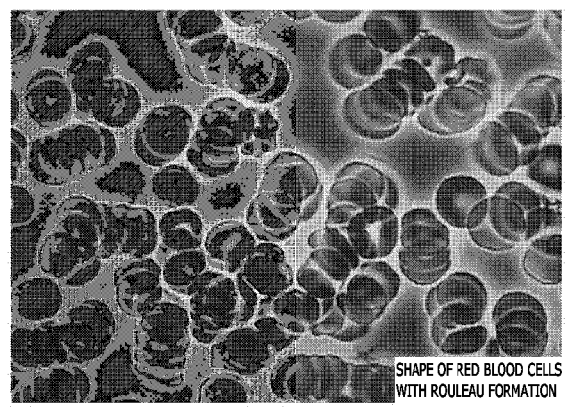
FIG. 9C is a view for explaining a stimulation related to improvement of Rouleaux formation as an example of a magnetic field stimulation by a dialyzer control apparatus according to an exemplary embodiment of the present disclosure.
Figure 9C:
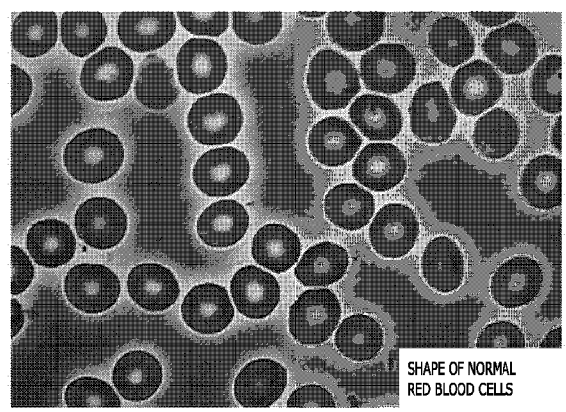

FIG. 9C is a view for explaining stimulation related to improvement of Rouleaux formation as an example of a magnetic field stimulation by a dialyzer control apparatus according to an exemplary embodiment of the present disclosure.

Specifically, in FIG. 9C, (a) is a view illustrating a shape of red blood cells in the blood with Rouleaux formation and (b) of FIG. 9C is a view illustrating a shape of red blood cells (shapes of normal red blood cells) when a magnetic field generated from the magnetic field generator 110 is applied to the blood with Rouleaux formation as illustrated in (a) of FIG. 9C.

Referring to FIG. 9C, it is confirmed that the blood with Rouleaux formation is formed by a long clot in which red blood cells are gathered together as illustrated in (a) of FIG. 9C. When a magnetic field generated from the magnetic field generator 110 is applied to the blood with Rouleaux formation, as illustrated in (b) of FIG. 9C, the red blood cells are formed so as not to overlap with each other. That is, the present apparatus 100 may provide an effect which stimulates the blood with the magnetic field generated from the magnetic field generator 110 to shake the red blood cells in the blood flowing into the dialyzer 1 to improve the Rouleaux formation.

Further, the present apparatus 100 may provide an effect which stimulates the blood with the magnetic field generated from the magnetic field generator 110 to accelerate metabolism by activating tissue cells. Further, the present apparatus 100 may provide an effect which stimulates the blood with the magnetic field generated from the magnetic field generator 110 to relieve various pains by stimulating a nervous system. The present apparatus 100 may apply a PEMF cell mechanism (in other words, a PEMF treatment mechanism) through a magnetic field generated from the magnetic field generator 110.

In the meantime, the controller 120 may change at least one type of magnetic field at every predetermined time interval. In other words, the controller 120 may change at least one type of a plurality of types (for example, an intensity, a frequency, a time, a pattern, and a stimulation mode of a magnetic field) of the magnetic field generated from the magnetic field generator 110 at every predetermined time interval. Here, the predetermined time may be set by seconds, such as two seconds, five seconds, or ten seconds. However, the present disclosure is not limited thereto and the predetermined time may be set by minutes or hours.

Further, the present apparatus 100 may include a hemoglobin level measuring unit (not illustrated) which measures a hemoglobin level (in other words, hemoglobin concentration) of red blood cells in the blood flowing into the dialyzer 1. The controller 120 may change the type of magnetic field from a first type to a second type depending on whether the hemoglobin level measured by the hemoglobin level measuring unit (not illustrated) is equal to or lower than a predetermined reference level.

For example, when the hemoglobin level of the red blood cells in the blood is equal to or lower than the predetermined reference level, the hemoglobin level measuring unit (not illustrated) may determine that the subject corresponding to the blood is anemia. As described above, when the hemoglobin level of the red blood cells in the blood is equal to or lower than a predetermined reference level (that is, it is determined to be anemia), the controller 120 may change the intensity of the magnetic field from the first type which has a weak intensity to the second type which has a strong intensity, among the types of magnetic field, so that more oxygen is quickly bond to the iron ions in the hemoglobin in the red blood cells. That is, the magnetic field generator 110 generates the magnetic field of the second type with a relatively strong intensity of magnetic field, rather than the first type with a relatively weak intensity of magnetic field, depending on whether the hemoglobin level of the red blood cells in the blood is equal to or lower than the predetermined reference level so that the present apparatus 100 may improve the anemia of the subject.

In this case, when the hemoglobin level measuring unit (not illustrated) determines whether the hemoglobin level of the red blood cells in the blood is equal to or lower than the predetermined reference level (that is, whether the subject is anemic), for example, subject information of the subject corresponding to the blood which has been already received may be considered. Here, the subject information which has been received may include a gender, an age, whether to be pregnant, and the like, but is not limited thereto.

A predetermined reference level of the hemoglobin level (hemoglobin concentration) according to a type of subject information (that is, a criterion for determining whether the subject is anemic) is as follows: for example, the hemoglobin level measuring unit (not illustrated) may determine that the subject is anemic when the measured hemoglobin level (in other words, a hemoglobin concentration) in the blood is lower than 13 g/dL for adult males, lower than 12 g/dL for adult females, lower than 12 g/dL for teenagers of 6 to 16 years old, lower than 11 g/dL for children of 6 months to 6 years old, and lower than 11 g/dL for a pregnant woman.

As described above, the controller 120 may determine whether the hemoglobin level of the red blood cells of the subject is equal to or lower than the predetermined reference level in consideration of the subject information which has been received and change the type of magnetic field generated from the magnetic field generator 110 depending on the determination result.

Further, the present apparatus 100 may include a core temperature measuring unit (not illustrated) which measures a temperature of the core 110a of the magnetic field generator 110. The controller 120 may control the type of magnetic field generated from the magnetic field generator 110 in consideration of whether the core temperature measured through the core temperature measuring unit (not illustrated) is equal to or higher than the predetermined reference temperature.

For example, when the core temperature measured by the core temperature measuring unit (not illustrated) is determined to be equal to or higher than a predetermined reference temperature, the controller 120 may change the intensity of the magnetic field as an example of the types of magnetic field, from a first type having a strong intensity to a second type having a weak intensity type so as to reduce the heat generated from the core. That is, depending on whether the core temperature is equal to or higher than the predetermined reference temperature, the magnetic field generator 110 generates the magnetic field by changing the first type with a relatively strong intensity of magnetic field to the second type with a relatively weak intensity of magnetic field so that the present apparatus 100 may be more safely driven.

As another example, when it is determined that the measured core temperature is equal to or higher than the predetermined reference temperature, the controller 120 may control to set a relatively low frequency or shorten the time to change the type of magnetic field generated from the magnetic field generator 110.

Hereinafter, various structures of the magnetic field generator 110 will be described. In other words, exemplary embodiments for various structures of the dialyzer 10 for improving Rouleaux formation including the magnetic field generator 110 proposed in the present disclosure will be described below.

In this case, even though some contents are omitted below, the contents which have been described for the magnetic field generator 110 may be applied to the following description for sub magnetic field generators 111, 112, 113, and 114, two magnetic field generators included in one pair of magnetic field generators 115, 115', 116, and 117, and three magnetic field generators included in the magnetic field generator 118 disposed with a triangular structure, respectively, in the same manner.

The magnetic field generator 110 according to a first exemplary embodiment of the present disclosure disposed on an outer surface of the dialyzer 1, for example, as illustrated in FIG. 8A, may be disposed on the outer surface of the dialyzer so that the dialyzer 1 is located by passing through a through hole of the core 110a included in the magnetic field generator 110. The structure of the magnetic field generator 110 as illustrated in FIG. 8A may be referred to as, for example, a dialyzer insertion type structure or a dialyzer insertion type cylindrical solenoid structure.

Figure 10A:
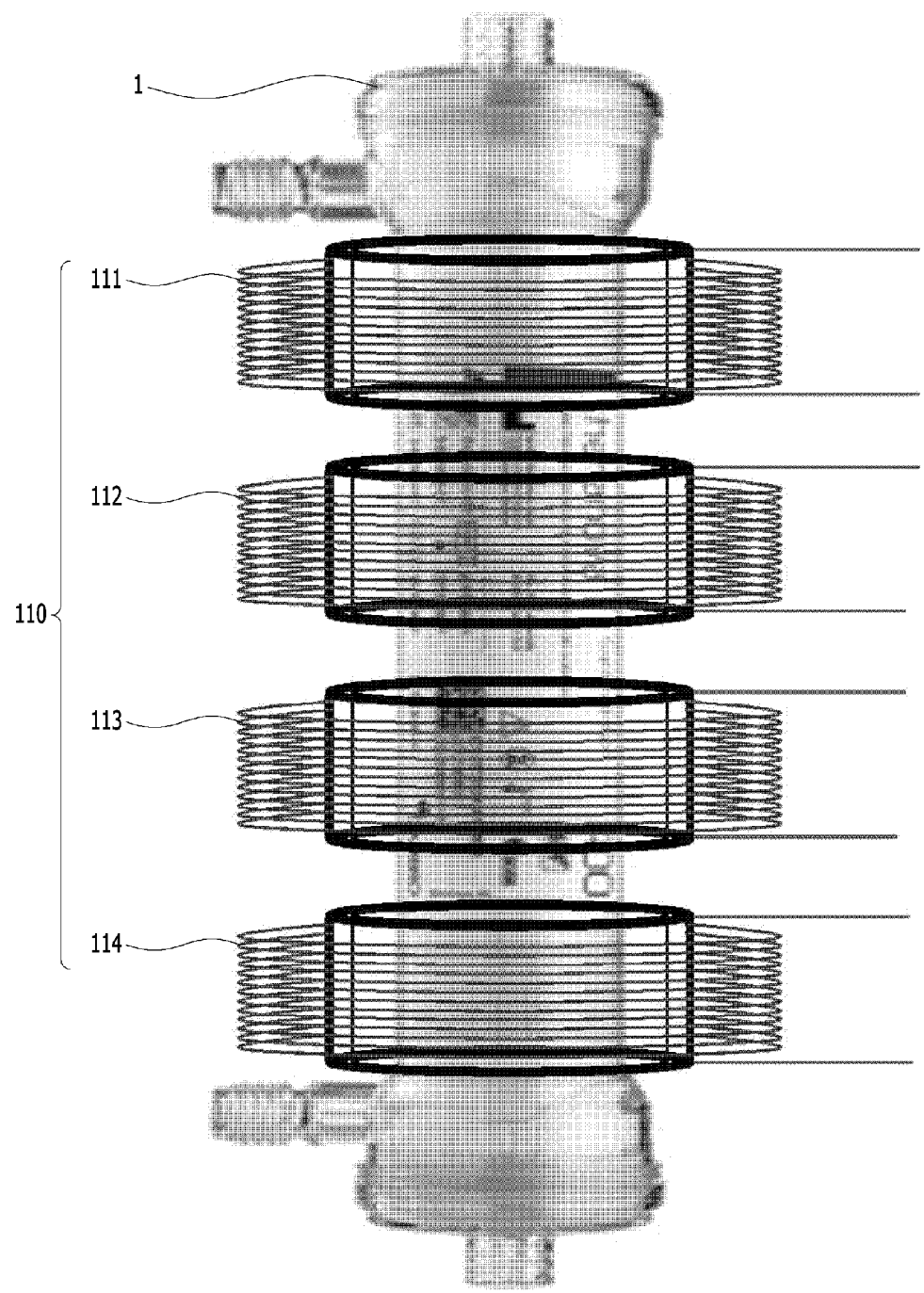
FIG. 10A is a view illustrating a structure of a magnetic field generator according to a second exemplary embodiment which is applied to a dialyzer control apparatus according to an exemplary embodiment of the present disclosure.

FIG. 10A is a view illustrating a structure of a magnetic field generator 110 according to a second exemplary embodiment which is applied to a dialyzer control apparatus 100 according to an exemplary embodiment of the present disclosure.

Referring to FIG. 10A, the magnetic field generator 110 according to the second exemplary embodiment of the present disclosure disposed on the outer surface of the dialyzer 1 may include a plurality of sub magnetic field generators 111, 112, 113, and 114 which is disposed with an interval along a length direction of the dialyzer 1. That is, the magnetic field generator 110 according to the second exemplary embodiment of the present disclosure may be formed by a structure in which N sub magnetic field generators are stacked with an interval along the length direction of the dialyzer 1.

In the example with reference to FIG. 10A, it is illustrated that as the plurality of sub magnetic field generators 111, 112, 113, and 114, four magnetic field generators are included (that is, N is 4), but the present disclosure is not limited thereto and the number of sub magnetic field generators may vary. For example, the structure of the magnetic field generator 110 as illustrated in FIG. 10A may be referred to as a dialyzer insertion type stack structure.

The controller 120 may control the types of the magnetic field generated from the plurality of sub magnetic field generators 111, 112, 113, and 114 in different ways, respectively. For example, the controller 120 may control a type of a magnetic field of a first sub magnetic field generator 111 as a first type, a type of a magnetic field of a second sub magnetic field generator 112 as a second type, a type of a magnetic field of a third sub magnetic field generator 113 as a third type, and a type of a magnetic field of a fourth sub magnetic field generator 114 as a fourth type. Here, for example, in the first type, a frequency of the magnetic field is 8 Hz, in the second type, a frequency of the magnetic field is 12 Hz, in the third type, a frequency of the magnetic field is 16 Hz, and in the fourth type, a frequency of the magnetic field is 20 Hz.

Further, the controller 120 may control at least some of the plurality of sub magnetic field generators 111, 112, 113, and 114 to be a first type and control the remaining sub magnetic field generators among the plurality of sub magnetic field generators 111, 112, 113, and 114 to be a second type. For example, the first sub magnetic field generator 111 and the fourth sub magnetic field generator 114 are controlled to be the first type and the second sub magnetic field generator 112 and the third sub magnetic field generator 113 are controlled to be the second type. Here, the first type may be a type having an intensity of magnetic field weaker than that of the second type and the second type may be a type having an intensity of magnetic field relatively stronger than that of the first type.

Figure 10B:
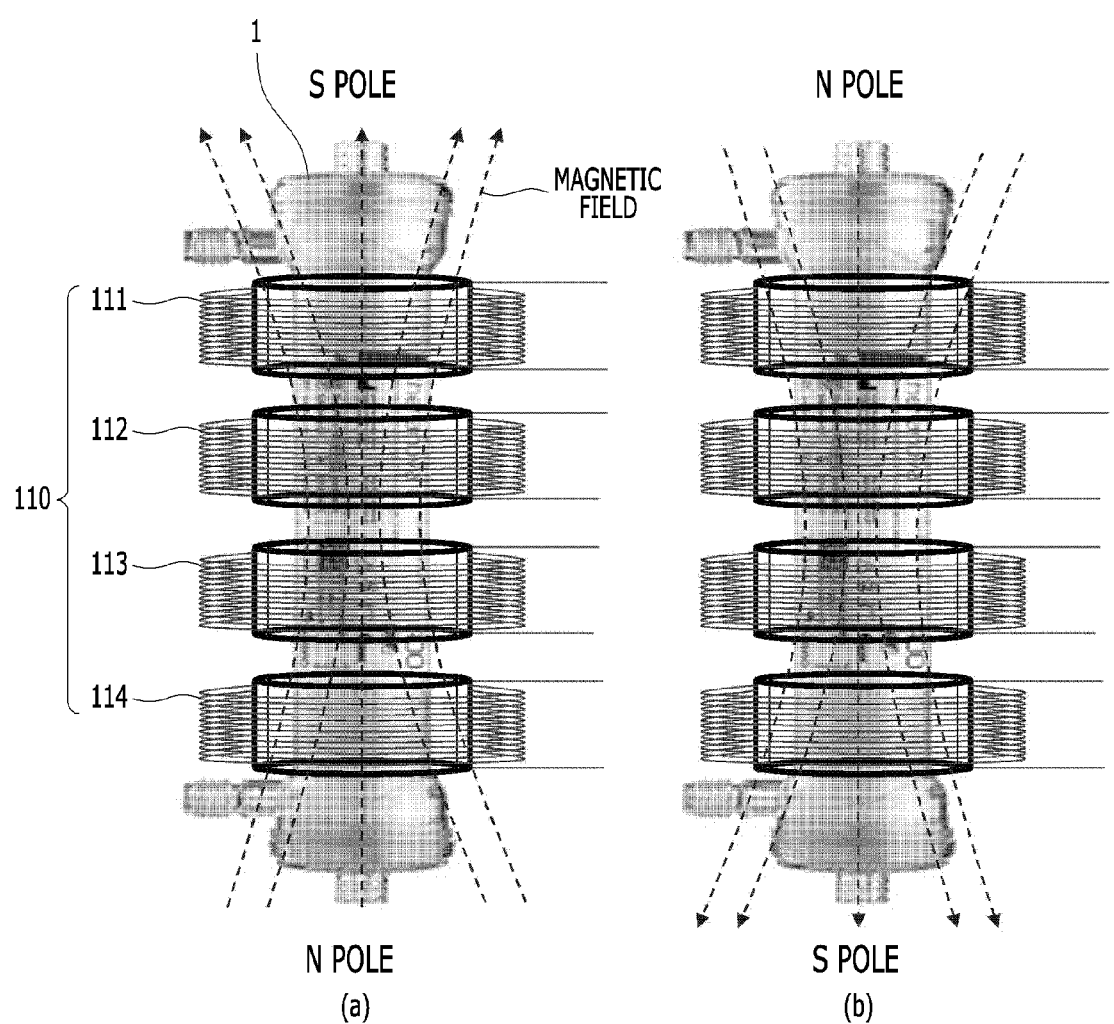
FIG. 10B is a view illustrating an example of a magnetic field generated from a magnetic field generator according to a second exemplary embodiment in a dialyzer control apparatus according to an exemplary embodiment of the present disclosure.

FIG. 10B is a view illustrating an example of a magnetic field generated from a magnetic field generator 110 according to a second exemplary embodiment in a dialyzer control apparatus 100 according to an exemplary embodiment of the present disclosure.

Referring to (a) of FIG. 10B, the controller 120 may control the magnetic field generator 110 including a plurality of sub magnetic field generators 111, 112, 113, and 114 so as to generate a magnetic field in which an N pole is formed at the lower side of the dialyzer 1 and an S pole is formed at the upper side of the dialyzer 1, for example, with reference to the drawing (that is, a magnetic field is formed from the lower side to the upper side of the dialyzer). Further, referring to (b) of FIG. 10B, the controller 120 may control the magnetic field generator 110 including a plurality of sub magnetic field generators 111, 112, 113, and 114 so as to generate a magnetic field in which an S pole is formed at the lower side of the dialyzer 1 and an N pole is formed at the upper side of the dialyzer 1, for example, with reference to the drawing (that is, a magnetic field is formed from the upper side to the lower side of the dialyzer).

Figure 11:
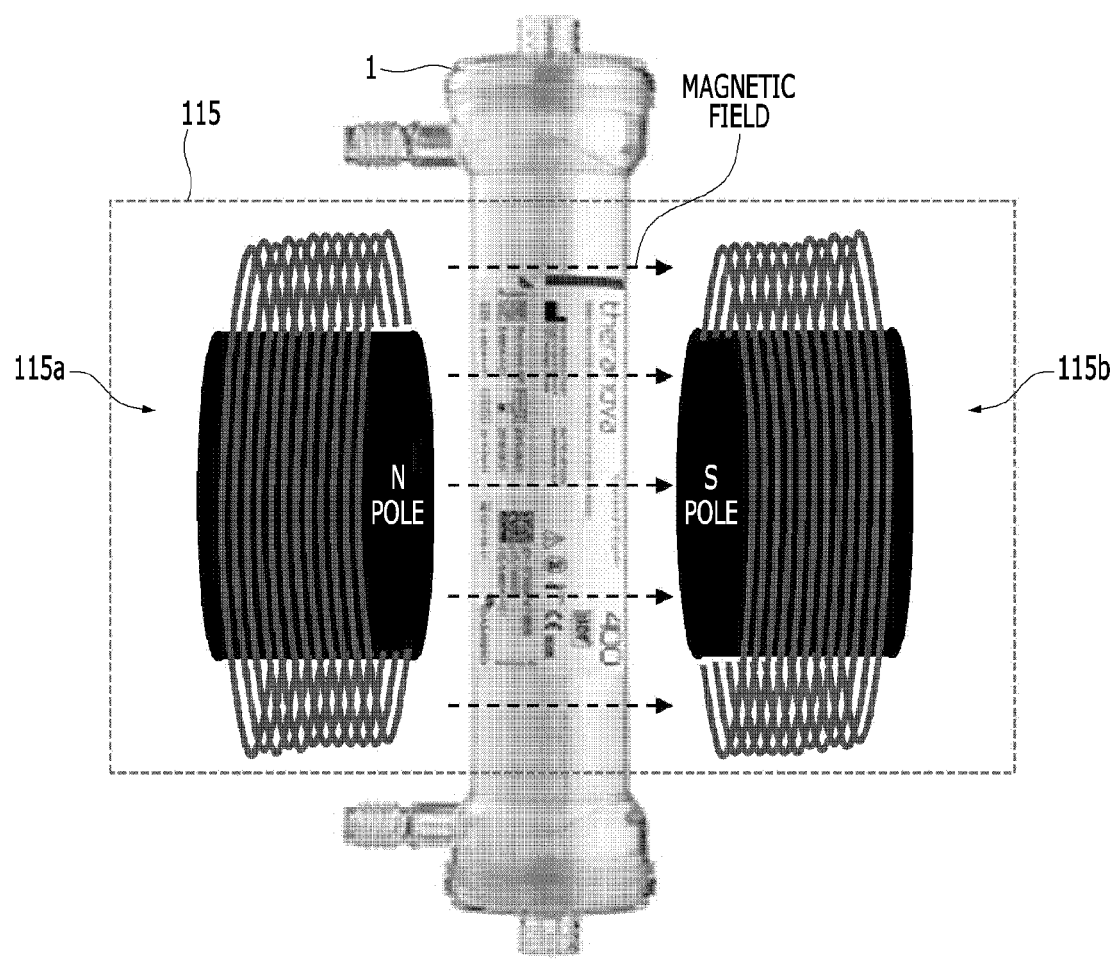
FIG. 11 is a view illustrating a structure of a magnetic field generator according to a third exemplary embodiment which is applied to a dialyzer control apparatus according to an exemplary embodiment of the present disclosure.

FIG. 11 is a view illustrating a structure of a magnetic field generator 110 according to a third exemplary embodiment which is applied to a dialyzer control apparatus 100 according to an exemplary embodiment of the present disclosure.

Referring to FIG. 11, the magnetic field generator 110 according to the third exemplary embodiment of the present disclosure disposed on the outer surface of the dialyzer 1 may include a pair of magnetic field generators 115 which are disposed to be opposite to each other with a circumference of the dialyzer 1 therebetween. Here, one pair of magnetic field generators 115 may include a first magnetic field generator 115a and a second magnetic field generator 115b.

For example, the controller 120 may control the types of the magnetic fields of the first magnetic field generator 115a and the second magnetic field generator 115b included in one pair of magnetic field generators 115 to be different from each other. For example, the controller 120 may control one pair of magnetic field generators 115 to allow the first magnetic field generator 115a to operate in an N pulse stimulation mode and the second magnetic field generator 115b to operate in an S pulse stimulation mode. In other words, the controller 120 may control one pair of magnetic field generators 115 to allow the first magnetic field generator 115a to generate an N pulse magnetic field and the second magnetic field generator 115b to generate an S pulse magnetic field.

Further, when the first magnetic field generator 115a between one pair of magnetic field generators 115 generates the N pulse stimulation as a type of magnetic field, the second magnetic field generator 115b between one pair of magnetic field generators 115 may generate the S pulse stimulation as a type of magnetic field. The controller 120 may control one pair of magnetic field generators 115 to allow the first magnetic field generator 115a and the second magnetic field generator 115b to alternately generate the N pulse stimulation and the S pulse stimulation according to a predetermined cycle. Here, the predetermined cycle may be set by seconds, minutes, hours, or the like. In this case, the description for one pair of magnetic field generator 115 may be applied to the description for the other pair of magnetic field generators 115', 116, and 117 in the same manner.

As another example, the magnetic field generator 110 disposed on the outer surface of the dialyzer 1 may be disposed such that a plurality of pairs of magnetic field generators is disposed to be opposite to each other with the circumference of the dialyzer 1 therebetween. This will be more easily understood with reference to FIG. 12.

Figure 12:
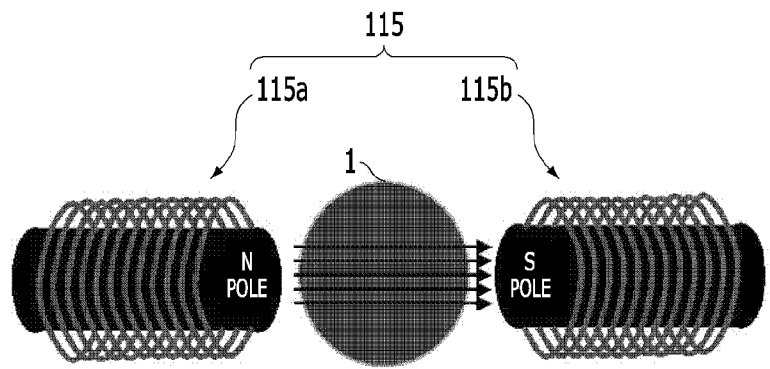
FIG. 12 is a view illustrating a structure of a magnetic field generator according to a third exemplary embodiment which is applied to a dialyzer control apparatus according to an exemplary embodiment of the present disclosure and an example that a plurality of magnetic field generators according to the third exemplary embodiment is provided.
Figure 12:
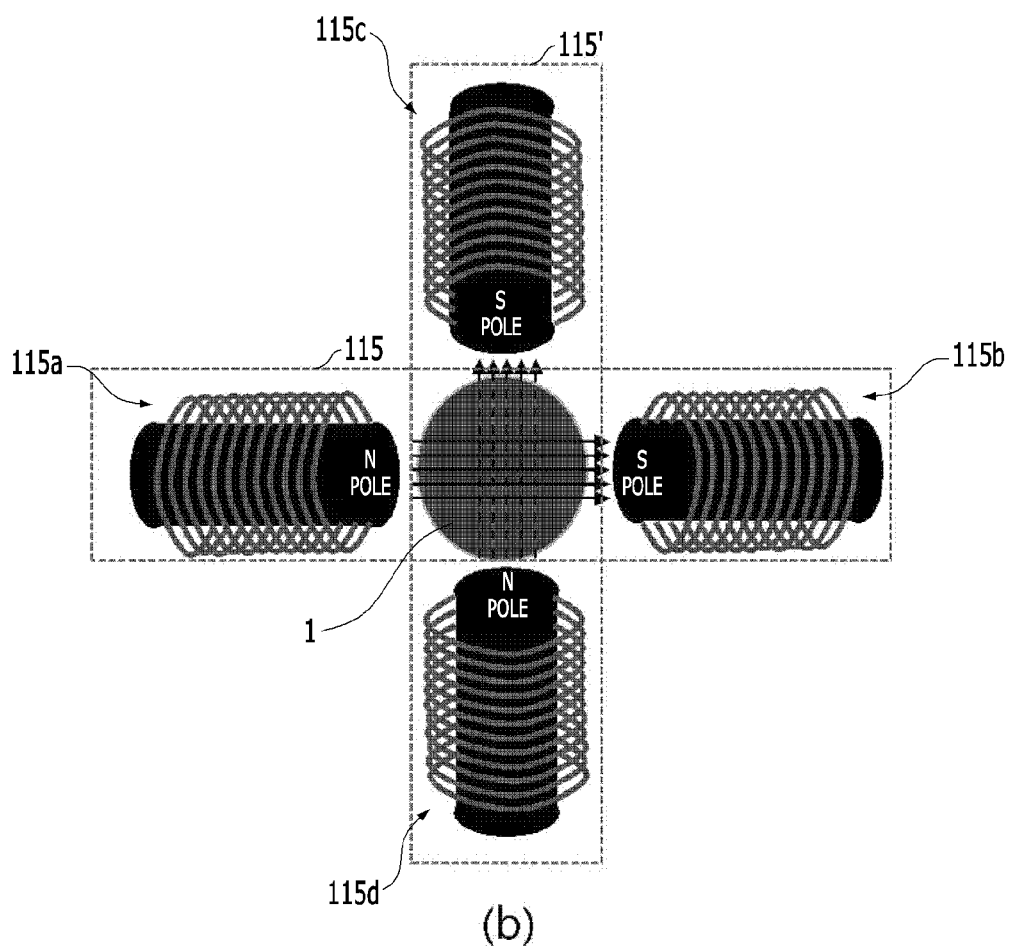

FIG. 12 is a view illustrating a structure of a magnetic field generator 110 according to a third exemplary embodiment which is applied to a dialyzer control apparatus 100 according to an exemplary embodiment of the present disclosure and an example that a plurality of magnetic field generators 110 according to the third exemplary embodiment is provided.

Referring to FIG. 12, specifically, (a) of FIG. 12 illustrates a plan view of a magnetic field generator 110 according to the third exemplary embodiment illustrated in FIG. 11. The magnetic field generator 110 according to the third exemplary embodiment of the present disclosure may be disposed such that one pair of magnetic field generators 115 including a first magnetic field generator 115a and a second magnetic field generator 115b is disposed to be opposite to each other with the circumference of the dialyzer 1 therebetween.

(b) of FIG. 12 illustrates a plan view of a plurality of pairs of generators 115 and 115' which is disposed to be opposite to each other with the circumference of the dialyzer 1 therebetween. Even though in (b) of FIG. 12, for example, two pairs of generators 115 and 115' are disposed to be opposite to each other with the circumference of the dialyzer 1 therebetween, the present disclosure is not limited thereto and the number of generators may vary.

When the plurality of pairs of magnetic field generators is disposed to be opposite to each other with the circumference of the dialyzer 1 therebetween as in (b) of FIG. 12, the controller 120 may respectively control the type of the magnetic field generated from the plurality of pairs of magnetic field generators 115 and 115' to be different from each other. That is, the controller 120 may control a type of the magnetic field generated from one pair of magnetic field generators 115 and a type of the magnetic field generated from the other pair of magnetic field generators 115' to be different from each other.

For example, the controller 120 may control one pair of magnetic field generators 115 to generate a magnetic field having a type of magnetic field with an intensity weaker than that of the other pair of magnetic field generator 115' and control the other pair of magnetic field generators 115' to generate a magnetic field having a type of magnetic field with an intensity stronger than that of one pair of magnetic field generators 115.

Further, the controller 120 may control one pair of magnetic field generators 115 to allow the first magnetic field generator 115a included in one pair of magnetic field generators 115 to generate an N pulse magnetic field and allow the second magnetic field generator 115b to generate an S pulse magnetic field. Further, the controller 120 may control the other pair of magnetic field generators 115' to allow the first magnetic field generator 115c included in the other pair of magnetic field generators 115' to generate an S pulse magnetic field and allow the second magnetic field generator 115d to generate an N pulse magnetic field.

Figure 13:
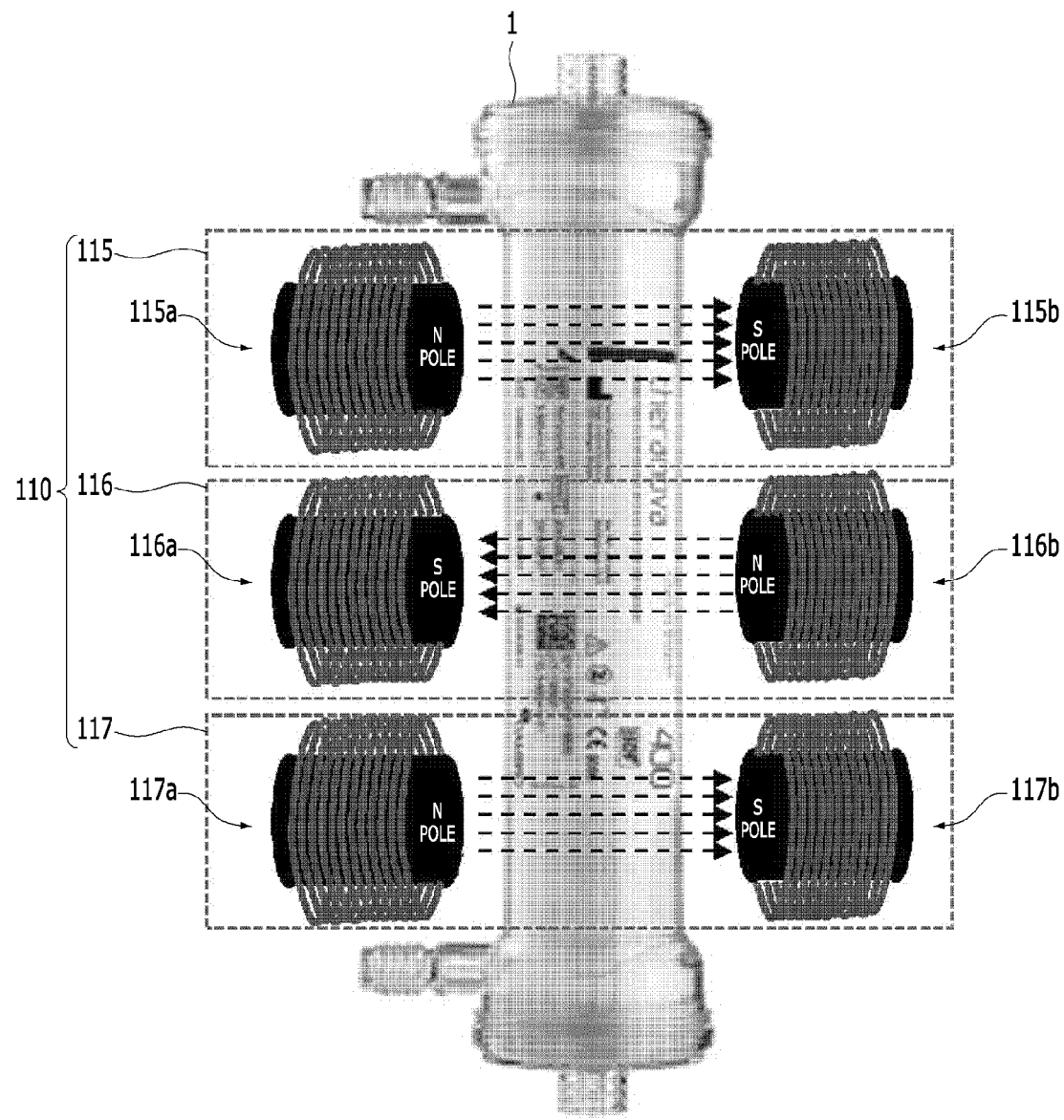
FIG. 13 is a view illustrating a structure of a magnetic field generator according to a fourth exemplary embodiment which is applied to a dialyzer control apparatus according to an exemplary embodiment of the present disclosure.

FIG. 13 is a view illustrating a structure of a magnetic field generator 110 according to a fourth exemplary embodiment which is applied to a dialyzer control apparatus 100 according to an exemplary embodiment of the present disclosure.

Referring to FIG. 13, a magnetic field generator 110 according to a fourth exemplary embodiment of the present disclosure disposed on the outer surface of the dialyzer 1 may include a plurality of pairs of magnetic field generators 115, 116, and 117 which are disposed with an interval along a length direction of the dialyzer 1. That is, the magnetic field generator 110 according to the fourth exemplary embodiment of the present disclosure may be formed by a structure in which N pairs of magnetic field generators are stacked with an interval along the length direction of the dialyzer 1.

In the example with reference to FIG. 13, it is illustrated that as the plurality of pairs of magnetic field generators 115, 116, and 117, three pairs of magnetic field generators are included (that is, N is 3), but the present disclosure is not limited thereto and the number of pairs of magnetic field generators may vary.

The controller 120 may control the type of the magnetic field generated from the plurality of pairs of magnetic field generators 115, 116, and 117 to be different from each other, respectively.

For example, the controller 120 may control the types of magnetic fields generated from the plurality of pairs of magnetic field generators 115, 116, and 117 to be different from each other such that another pair of magnetic field generators 116 generates a magnetic field with an intensity stronger than that of one pair of magnetic field generators 115 and the third pair of magnetic field generators 117 generates a magnetic field with an intensity stronger than that of another pair of magnetic field generators 116.

Further, for example, the controller 120 may control one pair of magnetic field generators 115 to allow the first magnetic field generator 115a included in one pair of magnetic field generators 115 to generate an N pulse magnetic field and allow the second magnetic field generator 115b to generate an S pulse magnetic field. Further, the controller 120 may control another pair of magnetic field generators 116 to allow the first magnetic field generator 116a included in another pair of magnetic field generators 116 to generate an S pulse magnetic field and allow the second magnetic field generator 116b to generate an N pulse magnetic field. Further, the controller 120 may control the third pair of magnetic field generators 117 to allow the first magnetic field generator 117a included in the third pair of magnetic field generators 117 to generate an N pulse magnetic field and allow the second magnetic field generator 117b to generate an S pulse magnetic field.

Further, the controller 120 may control the type of the magnetic field of the plurality of pairs of magnetic field generators 115, 116, and 117 to be different from each other to generate different types of pulses between one pair of magnetic field generators disposed up and down in the length direction of the dialyzer 1 with reference to FIG. 13.

For example, the controller 120 may collectively and simultaneously (together) control the plurality of magnetic field generators 115a, 115b, 116a, 116b, 117a, and 117b or individually control the plurality of magnetic field generators 115a, 115b, 116a, 116b, 117a, and 117b.

Figure 14:
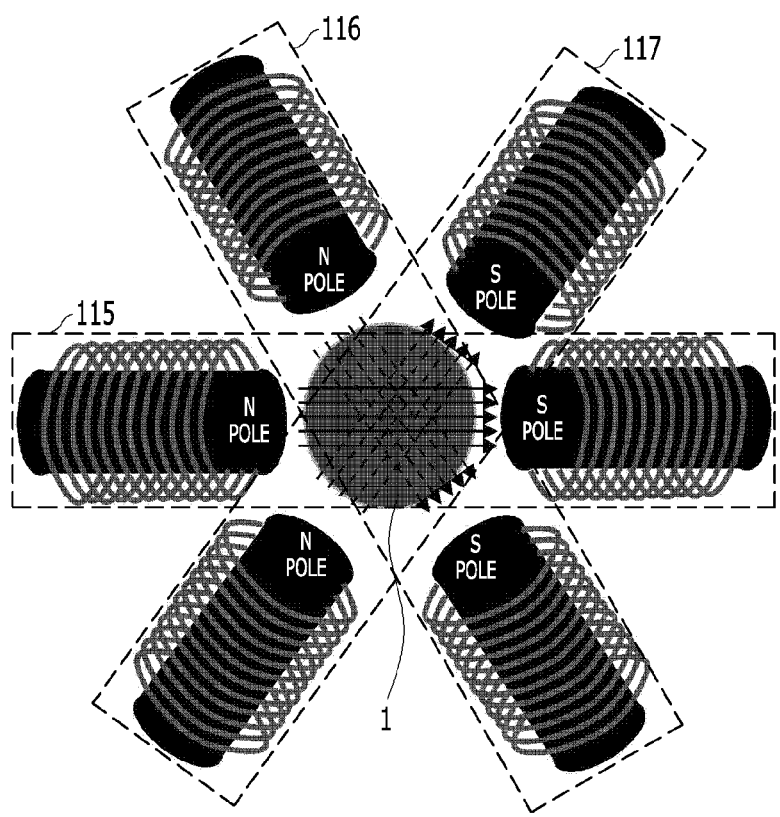
FIG. 14 is a view illustrating an example of a plan view of a magnetic field generator according to a fourth exemplary embodiment which is applied to a dialyzer control apparatus according to an exemplary embodiment of the present disclosure.

A plan view of the plurality of pairs of magnetic field generators 115, 116, and 117 disposed with an interval along the length direction of the dialyzer 1, that is, a plan view of the magnetic field generator 110 according to the fourth exemplary embodiment illustrated in FIG. 13 may be the same as (a) of FIG. 12 as an example, may be the same as (b) of FIG. 12 as another example, or may be the same as FIG. 14 as still another example.

FIG. 14 is a view illustrating an example of a plan view of a magnetic field generator 110 according to a fourth exemplary embodiment which is applied to a dialyzer control apparatus 100 according to an exemplary embodiment of the present disclosure.

Referring to FIG. 14, the plurality of pairs of magnetic field generators 115, 116, and 117 disposed with an interval along the length direction of the dialyzer may be disposed such that magnetic field stimulations are formed in different directions with respect to the circumference of the dialyzer 1 with reference to FIG. 14. However, the present disclosure is not limited thereto, but the plurality of pairs of magnetic field generators 115, 116, and 117 disposed with an interval along the length direction of the dialyzer, as illustrated in FIG. 12, may be disposed such that at least some of pairs of magnetic field generators form the magnetic field stimulation in the same direction with respect to the circumference of the dialyzer 1.

Figure 15:
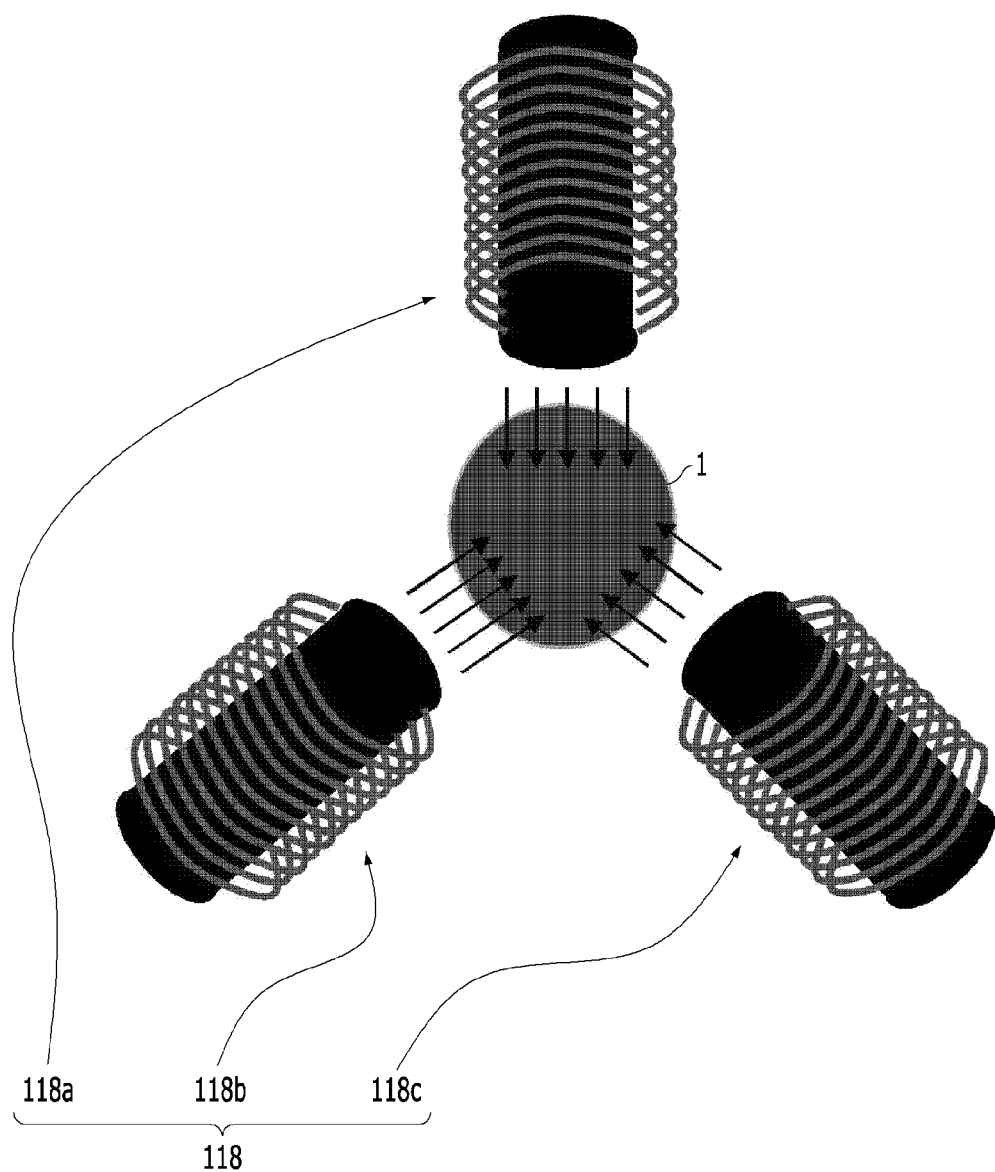
FIG. 15 is a view illustrating a structure of a magnetic field generator according to a fifth exemplary embodiment which is applied to a dialyzer control apparatus according to an exemplary embodiment of the present disclosure.

FIG. 15 is a view illustrating a structure of a magnetic field generator 110 according to a fifth exemplary embodiment which is applied to a dialyzer control apparatus 100 according to an exemplary embodiment of the present disclosure.

Referring to FIG. 15, a magnetic field generator 110 according to a fifth exemplary embodiment of the present disclosure disposed on the outer surface of the dialyzer 1 may include a plurality of sub magnetic field generators 118a, 118b, and 118c which is disposed with an interval with respect to the circumference of the dialyzer 1. That is, as the magnetic field generators 110 according to the fifth exemplary embodiment, N (for example, three) magnetic field generators may be disposed with an interval with respect to the circumference of the dialyzer 1. Here, in the example of FIG. 15, even though it is illustrated that the plurality of sub magnetic field generators 118a, 118b, and 118c is three, the present disclosure is not limited thereto and the number of sub magnetic field generators may vary.

For example, the plurality of sub magnetic field generators 118a, 118b, and 118c may be disposed with an interval of 120 degrees with respect to the circumference of the dialyzer 1. That is, the magnetic field generator 110 according to the fifth exemplary embodiment of the present disclosure may be formed with a structure in which three sub magnetic field generators 118a, 118b, and 118c are disposed with respect to the circumference of the dialyzer 1 with a triangular structure.

The controller 120 may control the type of the magnetic field(pulsed magnetic field) generated from the plurality of sub magnetic field generators 118a, 118b, and 118c to be different from each other, respectively.

In the meantime, in the above description, the structure of the magnetic field generator 110 as illustrated in FIG. 11 to FIG. 15, for example, may be referred to as an external symmetrical structure. Specifically, the structure of the magnetic field generator 110 as illustrated in FIG. 11 and (a) of FIG. 12 may be referred to as a two-balanced symmetrical structure, the structure of the magnetic field generator 110 as illustrated in (b) of FIG. 12 may be referred to as a four-square symmetrical structure, the structure of the magnetic field generator 110 as illustrated in FIG. 14 may be referred to as a six-hexagonal symmetrical structure, and the structure of the magnetic field generator 110 as illustrated in FIG. 15 may be referred to as a three-triangular structure.

The present apparatus 100 disposes the magnetic field generators 110 with various structures to perform the magnetic field stimulation so as to cover the entire internal area of the dialyzer 1. That is, the magnetic field stimulation may be more efficiently performed on the entire blood flowing into the dialyzer 1.

Further, the present apparatus 100 may include a distance adjusting unit (not illustrated) which adjusts a distance between one pair of magnetic field generators. The controller 120 may control the driving of the distance adjusting unit to adjust a type of magnetic field (for example, an intensity of the magnetic field) generated from one pair of magnetic field generators.

Specifically, referring to FIG. 11, the distance adjusting unit (not illustrated) may adjust the distance between the first magnetic field generator 115a and the second magnetic field generator 115b included in one pair of magnetic field generators 115 with the dialyzer 1 therebetween. This will be more easily understood with reference to FIG. 16.

Figure 16:
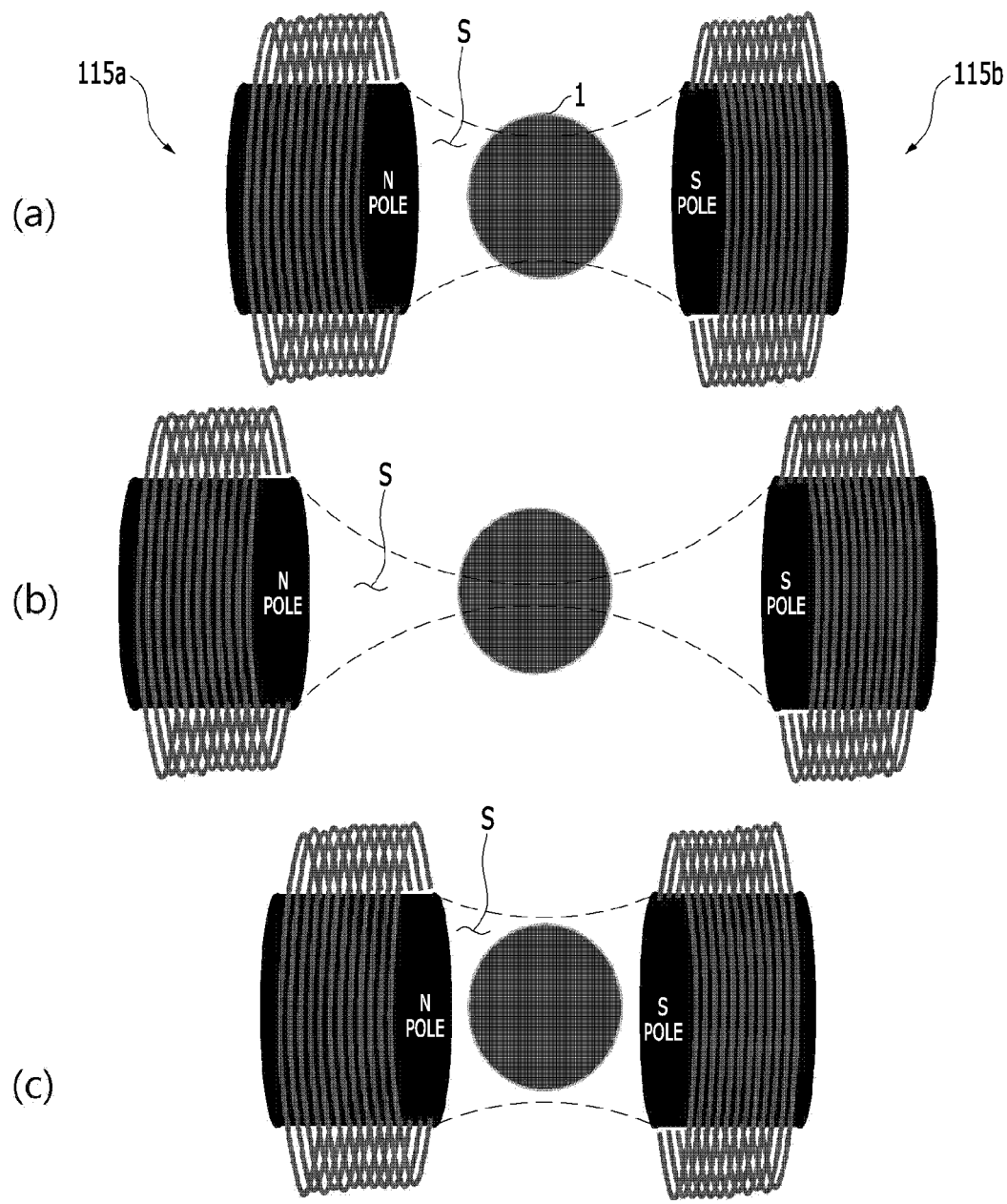
FIG. 16 is a view illustrating an example of adjusting a distance between one pair of magnetic field generators in a dialyzer control apparatus according to an exemplary embodiment of the present disclosure.

FIG. 16 is a view illustrating an example of adjusting a distance between one pair of magnetic field generators 115a and 115b in a dialyzer control apparatus 100 according to an exemplary embodiment of the present disclosure.

Referring to FIG. 16, in (b) of FIG. 16, the distance between one pair of magnetic field generators 115a and 115b is adjusted to be longer than that in (a) of FIG. 16. Referring to (c) of FIG. 16, the distance between one pair of magnetic field generators 115a and 115b is adjusted to be shorter than that in (a) of FIG. 16.

Referring to (b) of FIG. 16, it is confirmed that as the distance between one pair of magnetic field generators 115a and 115b with the dialyzer 1 therebetween is increased, an area S of the magnetic field formed between one pair of magnetic field generators 115a and 115b more deliberately concentrates and stimulates the blood in the dialyzer 1 in a narrow range with respect to the dialyzer 1. By doing this, the present apparatus 100 may intensively perform the magnetic field stimulation on the blood flowing into the dialyzer 1.

Referring to (c) of FIG. 16, it is confirmed that as the distance between one pair of magnetic field generators 115a and 115b with the dialyzer 1 therebetween is decreased, an area S of the magnetic field formed between one pair of magnetic field generators 115a and 115b stimulates the blood in the dialyzer 1 in a broad range with respect to the dialyzer 1. By doing this, the present apparatus 100 may broadly perform the magnetic field stimulation on the entire blood flowing into the dialyzer 1.

The distance adjusting unit (not illustrated), as illustrated in FIG. 11, not only adjusts the distance between the first magnetic field generator 115a and the second magnetic field generator 115b included in one pair of magnetic field generators 115, but also, as illustrated in FIG. 10A, adjusts the distance between the plurality of sub magnetic field generators 111, 112, 113, and 114 disposed with an interval along the length direction of the dialyzer 1. Further, the distance adjusting unit (not illustrated), as illustrated in (b) of FIG. 12, may adjust the distance between one pair of magnetic field generators 115 and the distance between the other pair of magnetic field generators 115' to be different from each other. Further, the distance adjusting unit (not illustrated), as illustrated in FIG. 13, may adjust not only the distance between a plurality of pairs of magnetic field generators 115, 116, and 117, but also the distance between two magnetic field generators included in each of the plurality of pairs of magnetic field generators 115, 116, and 117.

That is, the distance adjusting unit (not illustrated) may adjust the distance of the plurality of magnetic field generators with respect to the length direction of the dialyzer and/or adjust the distance with respect to the circumference of the dialyzer 1.

Further, the present apparatus 100 may include a power supply (not illustrated) which applies a power to the present apparatus 100 and a circuit which controls the generation of the frequency of the magnetic field generator 110.

Further, the present apparatus 100 may include a detector (not illustrated) which detects an over voltage (or over current) of a voltage (or current) supplied to the magnetic field generator 110. When the over voltage (or over current) is detected by the detector (not illustrated), the controller 120 may control a speaker (not illustrated) equipped in the present apparatus 100 to issue an alarm or control the magnetic field generator 110 not to generate the magnetic field. By doing this, the present apparatus 100 may allow a user who uses the present apparatus 100 to more safely use this apparatus 100.

Figure 17:
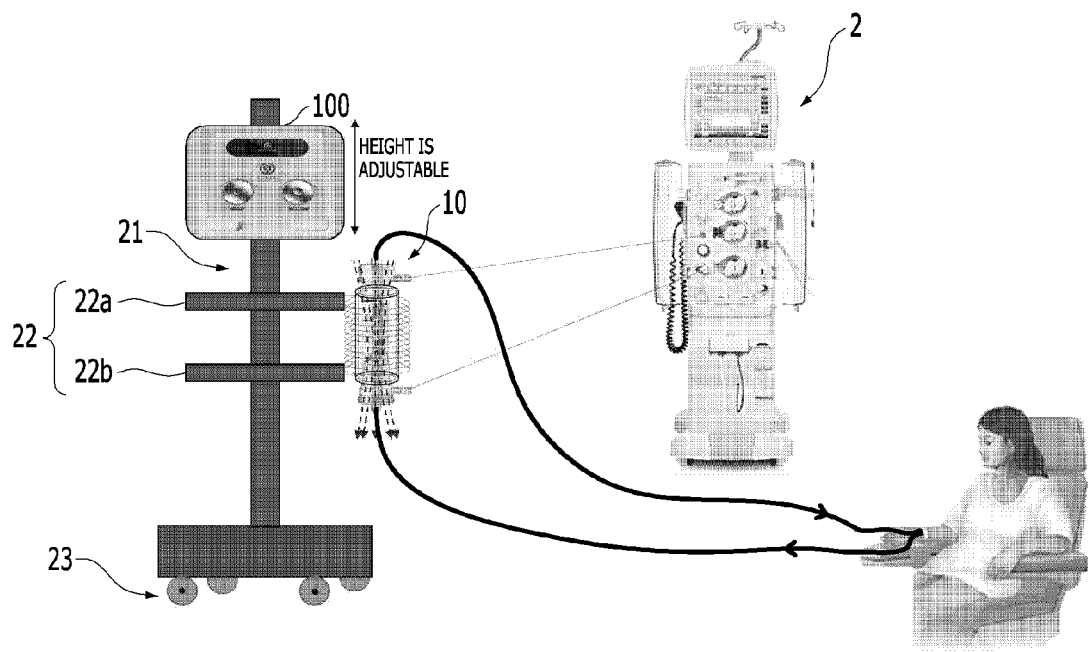
FIG. 17 is a view illustrating an example of a cradle of a dialyzer control apparatus according to an exemplary embodiment of the present disclosure and a dialyzer for improving Rouleaux formation.

FIG. 17 is a view illustrating an example of a stand type cradle on which a dialyzer control apparatus 100 according to an exemplary embodiment of the present disclosure and a dialyzer 10 for improving Rouleaux formation are mounted.

Referring to FIG. 17, the stand-type cradle on which the present apparatus 100 and the dialyzer 10 for improving Rouleaux formation proposed by the present disclosure are capable of being mounted may include a support portion 21 on which the present apparatus 100 is capable of being mounted and a mounting portion 22 on which the dialyzer 10 for improving Rouleaux formation is capable of being mounted.

With respect to the drawing, the support portion 21 may be provided in a vertical direction and the mounting portion 22 may be provided in a horizontal direction so as to intersect the support portion 21. For example, the mounting portion 22 may include, for example, a first mounting portion 22a and a second mounting portion 22b, but is not limited thereto.

In this case, the present apparatus 100 may be mounted on the support portion 21 and/or the dialyzer 10 for improving Rouleaux formation may be mounted on the mounting portion 22 by ring coupling, detachment, fitting, or the like, but is not limited thereto and the mounting may be performed by various coupling manners.

Further, the support portion 21 on which the present apparatus 100 is mounted may include a height adjusting member (not illustrated) which adjusts a height of the present apparatus 100. Further, the mounting portion 22 on which the dialyzer 10 for improving Rouleaux formation is mounted may be coupled to the support portion 21 so as to move vertically with respect to the support portion 21 and thus the height of the dialyzer 10 for improving Rouleaux formation may be adjusted.

Further, a moving member 23 may be provided on a lower surface of the stand-type cradle on which the present apparatus 100 and the dialyzer 10 for improving Rouleaux formation are mounted to allow the stand-type cradle to be movable. The moving member 23 may refer to a wheel and the like as an example.

In an example with reference to FIG. 17, it is illustrated that the present apparatus 100 and the dialyzer 10 for improving Rouleaux formation are mounted in the stand-type cradle which is provided separately from the hemodialysis apparatus 2 of the related art, but is not limited thereto. As another example, the present apparatus 100 and the dialyzer 10 for improving Rouleaux formation may be implemented to be mounted on the hemodialysis apparatus 2 of the related art. Further, according to the present disclosure, the existing dialyzer provided in the hemodialysis apparatus 2 of the related art may be easily replaced with the dialyzer 10 for improving Rouleaux formation proposed by the present disclosure, so that simple application and cost saving effects may be provided.

Hereinafter, an operation flow of the present disclosure will be described in brief based on the above-detailed description.

Figure 18:
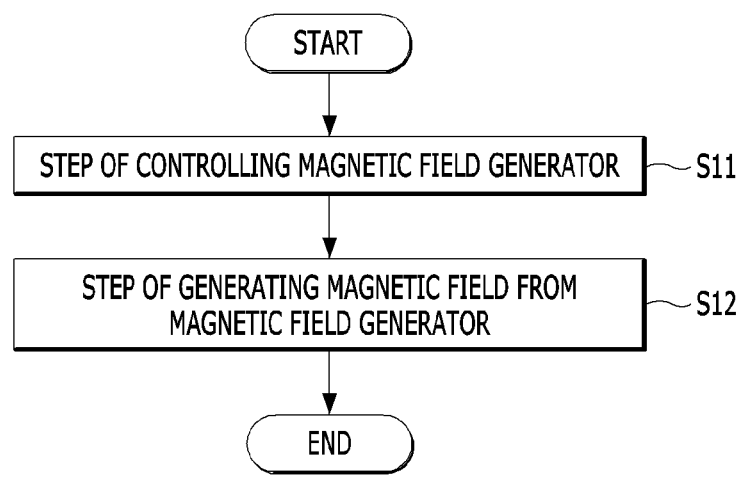
FIG. 18 is a flowchart of an operation of a driving method of a dialyzer control apparatus according to an exemplary embodiment of the present disclosure.

FIG. 18 is a flowchart of an operation of a driving method of a dialyzer control apparatus according to an exemplary embodiment of the present disclosure.

The driving method of the dialyzer control apparatus illustrated in FIG. 18 may be performed by the dialyzer control apparatus 100 (the present apparatus) which has been described above. Therefore, even though some contents are omitted below, the contents which have been described for the dialyzer control apparatus 100 (the present apparatus) may be applied to the description for the driving method of a dialyzer control apparatus in the same manner.

Referring to FIG. 18, in step S11, the controller 120 may control the magnetic field generator to perform magnetic field stimulation on the blood flowing into a dialyzer which removes wastes from the blood flowing therein to discharge.

Next, in step S12, a magnetic field may be generated from the magnetic field generator 110 provided to enclose an outer surface of the dialyzer in accordance with the control in step S11. In other words, in step S12, the magnetic field generator 110 may generate a magnetic field in accordance with the control in step S11. The magnetic stimulation for the blood flowing into the dialyzer may be performed by the magnetic field generated from the magnetic field generator 110.

In this case, the magnetic field stimulation may be a stimulation related to the improvement of the Rouleaux formation for the red blood cells in the blood. Further, the magnetic field stimulation may be a stimulation related to the blood ionization acceleration by coupling oxygen to iron ions included in the hemoglobin of the red blood cells. Further, the magnetic field stimulation may be a stimulation related to acceleration of at least one of anti-inflammatory, anti-cancer, and antimicrobial effects due to the production of nitric oxide (NO) in the blood.

Further, in step S11, the controller 120 may control at least one of an intensity, a frequency, a time, a pattern, and a stimulation mode of a magnetic field as a type of magnetic field generated from the magnetic field generator.

Further, in step S11, the controller may control the frequency of the magnetic field to be any one of 8 Hz to 30 Hz. Therefore, in step S12, the magnetic field generator generates a magnetic field with a frequency of any one of 8 Hz to 30 Hz to perform the magnetic field stimulation on the blood.

Further, even though not illustrated in the drawing, the driving method of a dialyzer control apparatus according to the exemplary embodiment of the present disclosure may further include a step of measuring a hemoglobin level of red blood cells in the blood flowing into the dialyzer by a hemoglobin level measuring unit (not illustrated). In this case, in step S11, the controller may change a type of a magnetic field generated from the magnetic field generator from a first type to a second type depending on whether the measured hemoglobin level is equal to or lower than a predetermined reference level.

Further, even though not illustrated in the drawing, the driving method of a dialyzer control apparatus according to the exemplary embodiment of the present disclosure may further include a step of measuring a core temperature of a magnetic field generator by a core temperature measuring unit (not illustrated). In this case, in step S11, the controller may control the type of the magnetic field generated from the magnetic field generator in consideration of whether the measured core temperature is equal to or higher than a predetermined reference temperature.

Further, in step S11, the controller may change at least one type of magnetic field at every predetermined time interval.

In step S11, the magnetic field generator may include a core having a through hole and a coil wound around the core. The magnetic field generator may be disposed on an outer surface of the dialyzer so that the dialyzer is located to pass through the through hole of the core included in the magnetic field generator and include a plurality of sub magnetic field generators disposed with an interval along the length direction of the dialyzer. In this case, in step S11, the controller may control the type of magnetic field generated from each of the plurality of sub magnetic field generators to be different from each other.

Further, the magnetic field generator may include one pair of magnetic field generators disposed to be opposite to each other with a circumference of the dialyzer therebetween. When a plurality of pairs of magnetic field generators disposed to be opposite to each other with a circumference of the dialyzer therebetween is provided, in step S11, the controller may control the types of the magnetic field generated from each of the plurality of pairs of magnetic field generators to be different from each other.

Further, the magnetic field generator may include a plurality of pairs of magnetic field generators disposed with an interval along the length direction of the dialyzer and in step S11, the controller may control the type of the magnetic field generated from the plurality of pairs of magnetic field generators to be different from each other.

Further, in step S12, when a first magnetic field generator between one pair of magnetic field generators generates an N pulse stimulation as a type of magnetic field, a second magnetic field generator between one pair of magnetic field generators may generate an S pulse stimulation as a type of magnetic field.

Further, in step S11, the controller may control one pair of magnetic field generators to allow the first magnetic field generator and a second magnetic field generator to alternately generate the N pulse stimulation and the S pulse stimulation according to a predetermined cycle.

Further, even though not illustrated in the drawing, the driving method of a dialyzer control apparatus according to the exemplary embodiment of the present disclosure may further include a step of adjusting a distance between one pair of magnetic field generators by a distance adjusting unit (not illustrated). In this case, in step S11, the controller may control the driving of the distance adjusting unit to adjust a type of the magnetic field generated from one pair of magnetic field generators.

In step S12, the magnetic field generator may generate a pulsed electro-magnetic field (PEMF).

In the above-description, steps S11 and S12 may be further divided into additional steps or combined as smaller steps depending on an implementation example of the present disclosure. Further, some steps may be omitted if necessary and the order of steps may be changed.

The method for driving a dialyzer control apparatus according to the exemplary embodiment of the present disclosure may be implemented as a program command which may be executed by various computer means to be recorded in a computer readable medium. The computer readable medium may include solely a program instruction, a data file, and a data structure or a combination thereof. The program instruction recorded in the medium may be specifically designed and constructed for the present disclosure or known to those skilled in the art of a computer software to be used. Examples of the computer readable recording medium include a magnetic media such as a hard disk, a floppy disk, or a magnetic tape, an optical media such as a CD-ROM or a DVD, a magneto-optical media such as a floptical disk, and a hardware device which is specifically configured to store and execute the program instruction, such as a ROM, a RAM, and a flash memory. Examples of the program instruction include not only a machine language code which is created by a compiler but also a high level language code which may be executed by a computer using an interpreter. The hardware device may operate as one or more software modules in order to perform the operation of the present disclosure and vice versa.

Further, the method for driving a dialyzer control apparatus may also be implemented as a computer program or an application executed by a computer which is stored in a recording medium.

The above-description of the present disclosure is illustrative only and it is understood by those skilled in the art that the present disclosure may be easily modified to another specific type without changing the technical spirit of an essential feature of the present disclosure. Thus, it is to be appreciated that the embodiments described above are intended to be illustrative in every sense, and not restrictive. For example, each component which is described as a singular form may be divided to be implemented and similarly, components which are described as a divided form may be combined to be implemented.

The scope of the present disclosure is represented by the claims to be described below rather than the detailed description, and it is to be interpreted that the meaning and scope of the claims and all the changes or modified forms derived from the equivalents thereof come within the scope of the present disclosure.

We claim:

1. A dialyzer control apparatus, comprising:
a magnetic field generator which is disposed on an outer surface of a dialyzer which removes wastes from a blood flowing therein to discharge and generates a magnetic field; and
a controller which controls the magnetic field generator to perform a magnetic field stimulation on the blood flowing into the dialyzer,
wherein the magnetic field stimulation includes a stimulation related to inhibition of Rouleaux formation for red blood cells in the blood, and
wherein the magnetic field generator includes one pair of magnetic field generators disposed to be opposite to each other with a circumference of the dialyzer therebetween and when there is a plurality of pairs of magnetic field generators disposed to be opposite to each other with the circumference, the controller controls the type of the magnetic field generated from each of the plurality of pairs of magnetic field generators to be different from each other.

2. The dialyzer control apparatus according to claim 1, wherein the magnetic field stimulation further includes a stimulation related to a blood ionization acceleration by binding oxygen to iron ions included in hemoglobin of the red blood cells.

3. The dialyzer control apparatus according to claim 1, wherein the magnetic field stimulation further includes a stimulation related to acceleration of at least one of anti-inflammatory, anti-cancer, and antimicrobial effects due to generation of nitric oxide (NO) in the blood.

4. The dialyzer control apparatus according to claim 1, wherein the magnetic field generator includes:
a core having a through hole; and
a coil wound around the core.

5. The dialyzer control apparatus according to claim 1, wherein the magnetic field generator is disposed on an outer surface of the dialyzer such that the dialyzer is located to pass through a through hole of a core included in the magnetic field generator, the magnetic field generator includes a plurality of sub magnetic field generators disposed with an interval along a length direction of the dialyzer, and the controller controls a type of magnetic field generated from each of the plurality of sub magnetic field generators to be different from each other.

6. The dialyzer control apparatus according to claim 1, wherein the magnetic field generator includes:
the plurality of pairs of magnetic field generators disposed with an interval along a length direction of the dialyzer and
the controller controls the type of the magnetic field generated from each of the plurality of pairs of magnetic field generators to be different from each other.

7. The dialyzer control apparatus according to claim 1, wherein when a first magnetic field generator between the one pair of magnetic field generators generates an N pulse stimulation as the type of the magnetic field, a second magnetic field generator between the one pair of magnetic field generators generates an S pulse stimulation as the type of the magnetic field and the controller controls the one pair of magnetic field generators to allow the first magnetic field generator and the second magnetic field generator to alternately generate the N pulse stimulation and the S pulse stimulation according to a predetermined cycle.

8. The dialyzer control apparatus according to claim 1, wherein the magnetic field generator generates a pulsed electro-magnetic field (PEMF).

9. The dialyzer control apparatus according to claim 1, further comprising:
a distance adjusting unit which adjusts a distance between the one pair of magnetic field generators.

10. The dialyzer control apparatus according to claim 9, wherein the controller controls driving of the distance adjusting unit to adjust the type of the magnetic field generated from the one pair of magnetic field generators.

11. The dialyzer control apparatus according to claim 1, wherein the controller controls at least one of an intensity, a frequency, a time, and a stimulation mode of the magnetic field as a type of the magnetic field generated from the magnetic field generator.

12. The dialyzer control apparatus according to claim 11, wherein the controller controls the frequency of the magnetic field to any one of 8 Hz to 30 Hz and the magnetic field generator generates the magnetic field having a frequency of any one of 8 Hz to 30 Hz to perform the magnetic field stimulation on the blood.

13. The dialyzer control apparatus according to claim 11, further comprising:
a hemoglobin level measuring unit which measures a hemoglobin level of red blood cells in the blood flowing into the dialyzer,
wherein the controller changes the type of the magnetic field from a first type to a second type depending on whether the measured hemoglobin level is equal to or lower than a predetermined reference level.

14. The dialyzer control apparatus according to claim 11, further comprising:
a core temperature measuring unit which measures a core temperature of the magnetic field generator,
wherein the controller controls the type of the magnetic field by considering whether the measured core temperature is equal to or higher than a predetermined reference temperature.

15. The dialyzer control apparatus according to claim 11, wherein the controller changes at least one type of the magnetic field at every predetermined time interval.

16. A driving method of the dialyzer control apparatus according to claim 1, the method comprising:
controlling the magnetic field generator to perform the magnetic field stimulation on the blood flowing into the dialyzer which removes wastes from the blood flowing therein to discharge; and
generating the magnetic field from the magnetic field generator provided to enclose the outer surface of the dialyzer according to the control.

17. The driving method according to claim 16, wherein during the controlling, at least one of an intensity, a frequency, a time, and a stimulation mode of the magnetic field is controlled as a type of the magnetic field generated from the magnetic field generator.

18. A non-transitory computer-readable storage medium that stores a program configured to implement the driving method of claim 16 on a computer.

19. A dialyzer control apparatus, comprising:
a magnetic field generator which is disposed on an outer surface of a dialyzer which removes wastes from a blood flowing therein to discharge and generates a magnetic field;
a hemoglobin level measuring unit which measures a hemoglobin level of red blood cells in the blood flowing into the dialyzer; and
a controller which controls the magnetic field generator to perform a magnetic field stimulation on the blood flowing into the dialyzer,
wherein the magnetic field stimulation is a stimulation related to inhibition of Rouleaux formation for red blood cells in the blood,
wherein the controller controls at least one of an intensity, a frequency, a time, and a stimulation mode of the magnetic field as a type of the magnetic field generated from the magnetic field generator, and
wherein the controller changes a type of the magnetic field from a first type to a second type depending on whether the measured hemoglobin level is equal to or lower than a predetermined reference level.

20. A dialyzer control apparatus, comprising:
a magnetic field generator which is disposed on an outer surface of a dialyzer which removes wastes from a blood flowing therein to discharge and generates a magnetic field;
a core temperature measuring unit which measures a core temperature of the magnetic field generator; and
a controller which controls the magnetic field generator to perform a magnetic field stimulation on the blood flowing into the dialyzer,
wherein the magnetic field stimulation is a stimulation related to inhibition of Rouleaux formation for red blood cells in the blood,
wherein the controller controls at least one of an intensity, a frequency, a time, and a stimulation mode of the magnetic field as a type of the magnetic field generated from the magnetic field generator, and
wherein the controller controls the type of the magnetic field by considering whether the measured core temperature is equal to or higher than a predetermined reference temperature.

* * * * *